US012752070B2

(12) United States Patent
Luo

(10) Patent No.: US 12,752,070 B2
(45) Date of Patent: Oct. 6, 2026

(54) CONNECTOR FOR A FRAME OF A RESPIRATOR

(71) Applicant: DCSTAR INC., New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/540,171

(22) Filed: Dec. 14, 2023

(65) Prior Publication Data

US 2025/0195818 A1 Jun. 19, 2025

(51) Int. Cl.
*A61M 16/08* (2006.01)
*A61M 16/06* (2006.01)

(52) U.S. Cl.
CPC .... *A61M 16/0816* (2013.01); *A61M 16/0616* (2014.02); *A61M 16/0633* (2014.02); *A61M 16/0683* (2013.01); *A61M 2205/42* (2013.01)

(58) Field of Classification Search
CPC .............. A61M 16/06; A61M 16/0605; A61M 16/0616; A61M 16/0622; A61M 16/0633; A61M 16/0638; A61M 16/0666; A61M 16/0683; A61M 16/0816; A61M 16/0825; A62B 18/084
See application file for complete search history.

(56) References Cited

U.S. PATENT DOCUMENTS 12,171,944 B1 * 12/2024 Luo ................... A61M 16/0825
12,239,790 B1 * 3/2025 Luo ....................... A61M 16/06
2014/0150798 A1 * 6/2014 Fong ................. A61M 16/0825 128/206.21
2014/0299134 A1 * 10/2014 Matula .............. A61M 16/0833 128/205.25
2018/0185598 A1 * 7/2018 Olsen ................ A61M 16/0875
2018/0236200 A1 * 8/2018 Goldspink ........ A61M 16/0057
2018/0250486 A1 * 9/2018 Amarasinghe .... A61M 16/0816
2019/0001094 A1 * 1/2019 Liu ................... A61M 16/0683
2021/0001072 A1 * 1/2021 Lim .................. A61M 16/0683
2021/0146083 A1 * 5/2021 Chang ............... A61M 16/0605
(Continued)

OTHER PUBLICATIONS

ItAll "Replacement Frame & Swivel Elbow Connector Set"; retrieved from https://www.amazon.com/Replacement-Connector-Compatible-Simplus%EF%BC%8CImproved-ItAll/dp/B0CQ1VKNVZ with product availability date of Dec. 13, 2023.*
(Continued)

*Primary Examiner* — Joseph D. Boecker
(74) *Attorney, Agent, or Firm* — HSML P.C.

(57) ABSTRACT

A connector can be installed on the frame of a mask assembly used for the treatment of sleep apnea. This connector can be detachably connectable to a mask and an elbow, making it compatible with various masks and elbows. The commonality of the connector offers more choices for patients. While ensuring effective exhaust, the connector is also easy to clean, reducing the risk of patients getting infections from mold and pathogens. The connector includes a first interface end, a second interface end, and an annular channel to connect to the first interface end and the second interface end. The axis of the connector coincides with the axis of the gas outlet of the elbow. The connector passes through the central opening of the frame and is securely connected to the frame.

25 Claims, 20 Drawing Sheets

(56) References Cited

U.S. PATENT DOCUMENTS

| | | | | |
|---|---|---|---|---|
| 2022/0134039 | A1 * | 5/2022 | Hartono | A61M 16/0616<br>128/206.24 |
| 2023/0263983 | A1 * | 8/2023 | Betteridge | A61M 16/0816<br>128/206.24 |
| 2024/0408337 | A1 * | 12/2024 | Wang | A61M 16/0816 |

OTHER PUBLICATIONS

Medihealer "Upgraded Frame Assembly" retrieved from https://www.amazon.com/Upgraded-Assembly-Compatible-Complete-Medihealer/dp/B0C7CH2VJQ with product availability date of Sep. 4, 2023.*

Medihealer "Replacement Frame Assembly" retrieved from https://www.amazon.com/Replacement-Assembly-Compatible-Including-Medihealer/dp/B0CLG8CCV2 with product availability date of Oct. 20, 2023.*

"Integrally" definition from Merriam-Webster Dictionary (retrieved from https://www.merriam-webster.com/dictionary/integrally).*

* cited by examiner

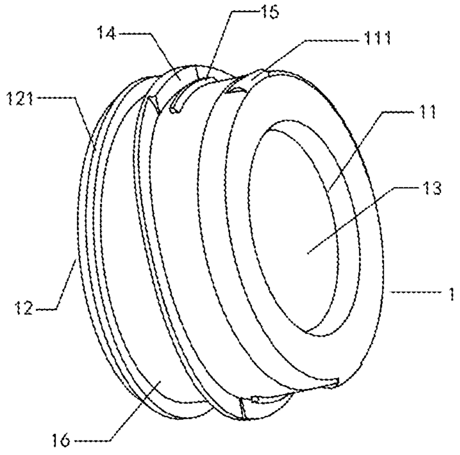
FIG.3A
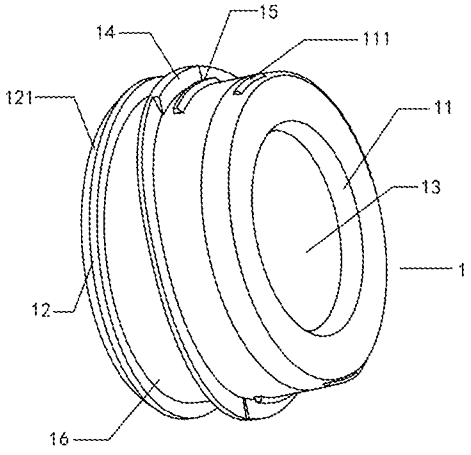
FIG.3B
Fig. 3

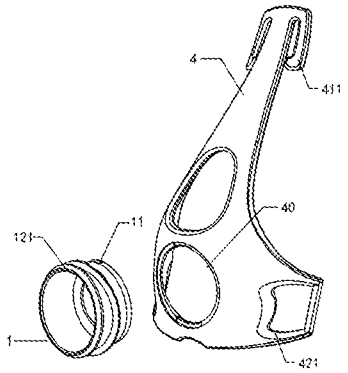
FIG.7A
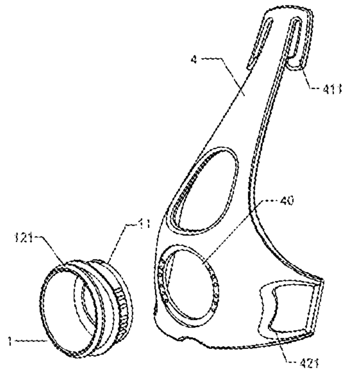
FIG.7B
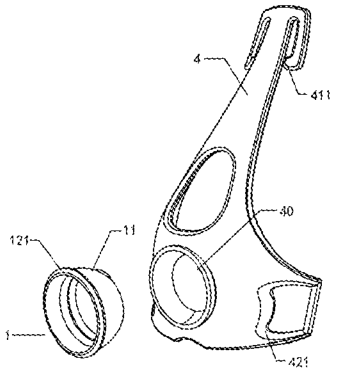
FIG.7C
Fig. 7

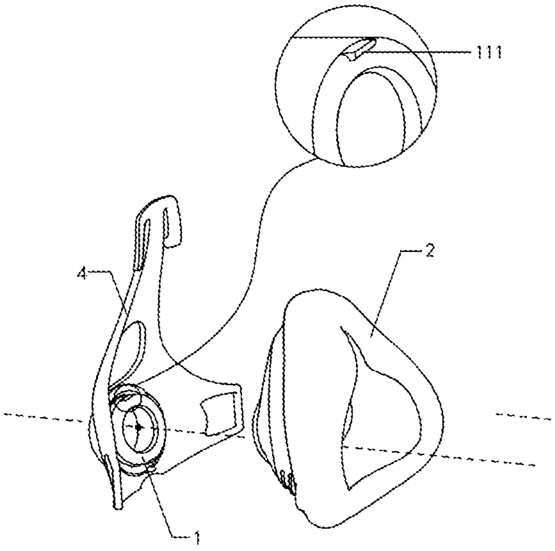
FIG.12A
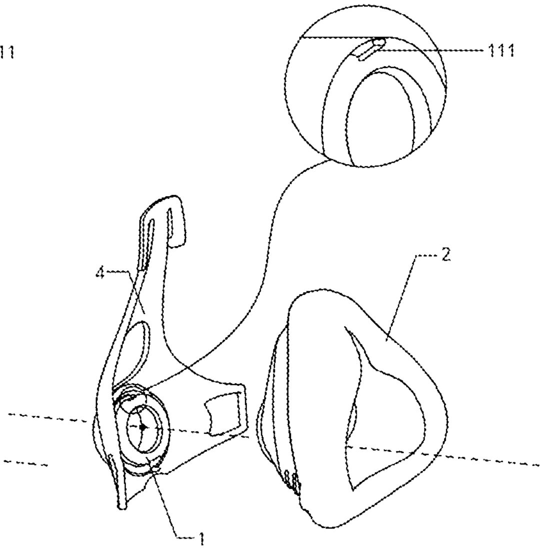
FIG.12B
Fig. 12

FIG.13A
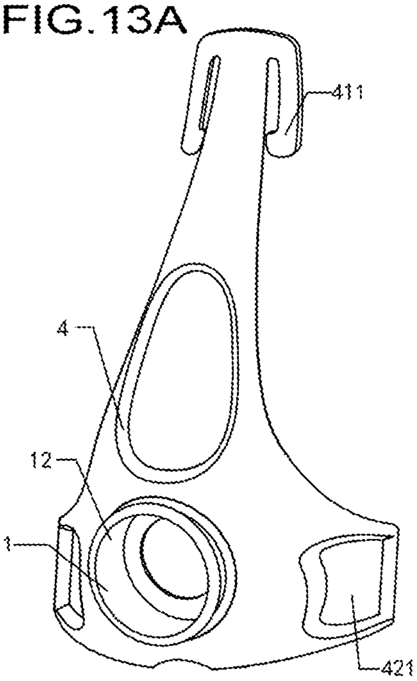
FIG.13B
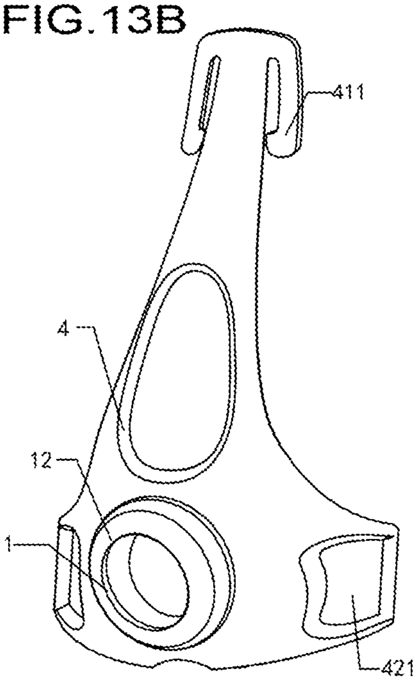
Fig. 13

CONNECTOR FOR A FRAME OF A RESPIRATOR

TECHNICAL FIELD

This disclosure pertains to the field of respiratory therapy technology, especially sleep breathing disorders such as Obstructive Sleep Apnea (OSA), specifically relating to a connector that is mounted on the frame of a face mask assembly used for treating sleep breathing disorders.

BACKGROUND

Sleep apnearapy is a crucial medical approach for alleviating sleep breathing disorders such as OSA, with common symptoms including nighttime apnea and snoring, daytime sleepiness and fatigue, and lack of concentration, all of which can severely impact a patient's health and quality of life and even increase the risk of chronic diseases like heart conditions, hypertension, and diabetes. Treatments for OSA include lifestyle changes and therapies using respiratory devices (like Continuous Positive Airway Pressure, or CPAP), and so on. In particular, CPAP is a prevalent treatment method that maintains the patient's upper airway's patency through a steady airflow pressure, preventing the occurrence of apneas, thereby enhancing sleep quality and alleviating related symptoms. Its specific form involves connecting the airway through a mask, nasal mask, or nasal pillow-type patient interface equipment. The positive air pressure continuously outputted by the CPAP device normally flows through a hose and an elbow, reaching the sealed air chamber formed together by the mask and frame, and non-invasively entering the airway. The seal and comfort of the face mask are critical to the treatment, and the frame, along with related connectors, are vital structural components influencing the face mask's seal and comfort.

The process of delivering a continuous and stable positive air pressure from a ventilator passing through a hose first, then passing through an elbow, and finally reaching the sealed area where the face mask meets the face involves three components: the bend, the frame, and the face mask. These components can be joined in several different ways, and different joining methods may lead to some leakage of airflow towards the gaps between two of the components. The fundamental requirements for parts involved in the airflow passage are good sealing, reliability, long life, a compact structure and simplicity in the system. During respiratory therapies, individuals' facial features, perceptions of pressure and the perception of the part of the face mask that makes contact vary. Patients need to select an appropriate breathing face mask based on their facial features and perceptions of pressure and the comfort of a face mask when using the face mask assembly. However, existing face mask frames can only accommodate one type of face mask and elbow, lacking designs of a face mask assembly that can be easily adjusted and replaced to meet different patients' needs.

Additionally, the exhaust port, as an indispensable part of most therapeutic device components, is used to expel waste gases such as carbon dioxide exhaled by the patient. The placement and design of the exhaust port directly affect the flow of air and the patient's breathing experience. In current designs, the exhaust port is usually located on the face mask or elbow. When the exhaust port is directly set on the face mask, the position of the exhaust port may cause airflow disturbances and noise due to the inconsistency of the exhaled gas direction, affecting the patient's sleep quality and treatment. The existing placement and design of the exhaust port may also lead to poor airflow or increased exhalation resistance. However, setting the exhaust port on the elbow can prevent the accumulation of carbon dioxide or other exhaled waste gases in the sealed air chamber. However, traditional respiratory face mask systems often have the exhaust port integrated into the elbow or the face mask, and they are molded as one piece. When patients need to replace the exhaust port, they have no choice but to replace the entire face mask or the elbow, which is not only environmentally unfriendly but also highly uneconomical for patients. Furthermore, having an exhaust port on the elbow or face mask is not conducive to adding a corresponding noise reduction function.

SUMMARY

Based on the background above, the disclosure provides a connector for a frame of a respirator, which uses a detachable connection method to assemble with the mask and elbow. This connector can be detachably connectable to face masks and elbows, adapts to different face masks and elbows, has great commonality and therefore provides more choices for patients. While ensuring the exhaust effect, it is easy to clean and can reduce the risk of patients getting infected with molds and other pathogens.

In an embodiment, a connector for a frame of a respirator is provided. The connector for a frame of a respirator is configured to link a face mask assembly and create a pathway to transmit positive pressure air or breathable air, including a first interface end for assembling with and communicating with a face mask, a second interface end for assembling with and communicating with an elbow, and an annular passage connecting the first interface end and the second interface end, allowing pressurized air to pass through and enter the airway. The axis of the connector coincides with the axis of a gas outlet at the elbow, with the connector passing through the central opening of the frame and being fixedly connected to the frame to prevent sliding or rotation of the connector relative to the frame.

In one embodiment, an overall length of the connector is greater than a wall thickness of the central opening of the frame.

In one embodiment, the first interface end is detachably connectable to the face mask, and the second interface end is detachably connectable to the elbow, with the connector connecting to both the elbow and face mask to form a seal.

In one embodiment, an outer periphery of the second interface end is smaller than an outer periphery of the first interface end.

In one embodiment, a central axis of the connector is configured to form an angle of at or between 10° to 90° with a symmetrical axis of the frame.

In another embodiment, a connector for a frame of a respirator is provided. The connector for a frame of a respirator is configured to connect to a face mask assembly and create a pathway to transmit positive pressure air or breathable air, including a first interface end for assembling with and communicating with a face mask, a second interface end for assembling with and communicating with an elbow, and an annular passage connecting the first interface end and the second interface end, allowing pressurized air to pass through and enter the airway. The axis of the connector coincides with the axis of a gas outlet at the elbow, with the connector passing through the central opening of the frame and being fixedly connected to the frame to prevent sliding or rotation of the connector relative to the frame. The length of the connector is at or between 3 to 50 mm; the inner diameter of the connector does not exceed 80 mm; the minimum ratio between the opening area of the second interface end and the outer surface area of the frame is 1:20.

In one embodiment, the frame is made from rigid or semi-rigid material.

In one embodiment, at least a portion of the frame contacts a face, and the frame is configured to cover at least a portion of the face mask when the frame and the face mask are connected.

In one embodiment, a gasket is provided on the connector between the first interface end and the second interface end, and a notch is provided on the edge of a central opening of a frame on the side facing the second interface end of the connector. The gasket is embedded in the notch when the connector is assembled with the frame.

In one embodiment, the outer surface of the first interface end has a first protrusion, and the outer surface of the second interface end has a second protrusion. A positioning protrusion is provided between the first protrusion and the gasket, and a positioning groove that corresponds to a concave-convex shape of an inner edge of the central opening of the frame is provided between the positioning protrusion and the gasket, and at least one side of the positioning protrusion, near the second interface end or away from the second interface end, is a sloped surface.

In one embodiment, one or more interlocking interfaces that mate with the second protrusion to form a sealed connection are provided at the central opening of the frame.

In another embodiment, a connector for a frame of a respirator is provided. The connector for a frame of a respirator is configured to connect to a face mask assembly and create a pathway to transmit positive pressure air or breathable air. The connector, configured for a removable attachment to a frame in a face mask assembly via insertion or surface contact, includes a first interface end for assembling with and communicating with a face mask, a second interface end for assembling with and communicating with an elbow, and an exhaust port that permeates an inner surface of the connector and an outer surface of the connector, communicating with an external environment to allow internal gas to flow out. An outer periphery of a section in which the connector fits with the frame is smaller than an inner periphery of a central opening of the frame configured to accommodate the connector. The exhaust port has at least one of the following characteristics: there being at least one exhaust port, diameters of two ends of one exhaust port being different, and a total area of the exhaust port accounting for at or between 3% to 90% of an external surface area of the connector.

In one embodiment, when the number of the exhaust port is more than one, each of the exhaust ports is distributed evenly or unevenly along an annular passage of the connector.

In one embodiment, the angle between the axis of the exhaust port and the axis of the connector is at or between 00 to 90°.

In one embodiment, the exhaust port is configured to be circular, oval, semicircular, or square.

In another embodiment, a connector for a frame of a respirator is provided. The connector for a frame of a respirator is configured to connect to a face mask assembly and create a pathway to transmit positive pressure air or breathable air. The connector, configured for a removable attachment to a frame in a face mask assembly by insertion or surface contact, includes a first interface end for assembling with and communicating with a face mask, a second interface end for assembling with and communicating with an elbow, and an exhaust port that permeates an inner surface of the connector and an outer surface of the connector, communicating with an external environment to allow internal gas to flow out. The exhaust port is distributed along the annular passage of the connector. An outer surface of the connector includes noise reduction components, which include noise reduction materials set for a corresponding exhaust port, with the noise reduction materials having at least one of the following characteristics: a density of the noise reduction material being at or between 0.8 to 1.8 g/cm$^3$, a surface area of the noise reduction material occupying at or between 3% to 90% of an outer surface area of the connector, a thickness of the noise reduction material being at or between 0.1 to 0.5 mm, and a weight range for noise reduction materials being at or between 0.02 to 0.2 grams.

In one embodiment, the noise reduction material is a mesh-like structure or a cotton fluff structure.

In one embodiment, the noise reduction material consists of cotton, nylon, or natural fabric.

In one embodiment, the noise reduction component is a mesh-like structure, a grille-like structure, or a partition with several micro-holes; the noise reduction component used for covering the exhaust port on the connector is made from material selected from polypropylene, polyethylene, polyester, nylon, or natural fabric.

In one embodiment, the noise reduction component includes an external connecting part, which connects to the connector through a snap-fit or a magnetic attraction.

In another embodiment, a connector or a frame of a respirator is provided, the connector or a frame of a respirator is configured to connect to a face mask assembly and create a pathway to transmit positive pressure air or breathable air. The connector, configured for a removable attachment to a frame in a face mask assembly by insertion or surface contact, includes a first interface end for assembling with and communicating with a face mask, a second interface end for assembling with and communicating with an elbow, and an exhaust port that permeates an inner surface of the connector and an outer surface of the connector, communicating with an external environment to allow internal gas to flow out. The exhaust port is distributed along the annular passage of the connector. The connector has at least one of the following characteristics: a volume ratio of the connector to the frame being at or between 1:1.8 to 1:14, a length of the connector being at or between 1 to 100 mm, and a weight of the connector being at or between 1 and 5 grams.

In one embodiment, an outer diameter of the first interface end is at or between 10 to 80 mm, an outer diameter of the second interface end is at or between 10 to 80 mm, and a wall thickness of the connector is at or between 0.3 to 5 mm.

In one embodiment, at least one end section of the connector has a circular cross-section.

In one embodiment, the connector is at least partially deformable.

In one embodiment, the connector is made from one or two materials selected from polycarbonate, polyethylene, polypropylene, and silicone.

In one embodiment, a face mask assembly includes the connector, the frame, the face mask, and the elbow. The connector is detachably connectable to the frame through a snap-fitting, a rotary fitting, or a magnetic attraction, or the connector securely connects to the frame by ultrasonic bonding or adhesive. The connector is connected to the face mask by a snap-fitting, a rotary fitting, or a magnetic attraction, and the connector is connected to the elbow through a snap-fitting, a ball socket rotation, or a hinge connection.

Implementing the connector for a frame of a respirator of this disclosure has at least the following beneficial effects:

1. Compatible with face masks and/or elbows of different functions, structures, and models, the connector for a frame of a respirator of this disclosure reduces research and development costs, a shortened development cycle, and saves materials: the modular design that the connector and frame are produced independently and then combined realizes the detachable connection between the frame, the face mask and the elbow, making it easy for patients to adapt the frame to different types of face masks or elbows by replacing different types of connectors for different situations. The modular design makes the connector an independent module relative to various parts of the respirator, which can be designed, developed, tested, and maintained separately, meaning that modifications and replacements of the connector only require changes to the corresponding connector without affecting the entire system, thereby saving materials and production costs and facilitating product maintenance. The design of the detachable connector helps to save the product's research and development time costs and shorten the manufacturing cycle, making it easier to improve product quality and flexibility to respond to rapid market changes.
2. Easy maintenance and low manufacturing costs: The separate mold design of the connector also reduces the complexity of the face mask assembly, making the entire product more controllable for patients. The face mask assembly is divided into several separate modules, making it easier to isolate and resolve issues with one module when there is dysfunction, thereby reducing the risk of dysfunction and alleviating the adverse impact during the replacement. Therefore, being green and sustainable, the design of the connector helps to protect the environment and save resources. Separating the design of the frame and the connector simplifies the structure, making mold manufacturing correspondingly simple, reducing corresponding mold manufacturing costs, shortening production cycles, and saving R&D cycles and costs.
3. Easy to clean: Attaching the connector to the frame together forms a modular exhaust connector. When patients clean the assembly, compared with a non-detachable assembly, the detachable structure does not have a complex structure, making cleaning more effective and simpler, reducing the probability of bacterial growth, and protecting the patients from infection.
4. By separating the exhaust port from the face mask or elbow, forming a connector that is individually replaceable, and has an exhaust port, and separately molding the connector and then securely attaching it to the frame, patients can meet different needs for the exhaust port by replacing the corresponding connector. The modular design of the connector allows patients to focus on specific connectors rather than the entire respiratory system, enables quick replacement and rapid adaptation to new face masks or elbows emerging on the market, enhances the universality and reliability of the connectors, and reduces the rate at which patients discard respiratory accessories, therefore decreasing carbon emissions, exerting a beneficial impact on climate change and helping to protect the environment.

BRIEF DESCRIPTION OF THE DRAWINGS

FIG. 3A and FIG. 3B are schematic diagrams of the connector in accordance with multiple embodiments;

FIG. 7A, FIG. 7B and FIG. 7C are schematic diagrams showing different methods of connecting the connector and frame in accordance with an embodiment;

FIG. 12A and FIG. 12B are schematic diagrams showing the structure of the connector fitting with the face mask in accordance with an embodiment;

FIG. 13A and FIG. 13B are schematic diagrams showing several different structures of the connector in accordance with an embodiment;

DETAILED DESCRIPTION

Figure 1:
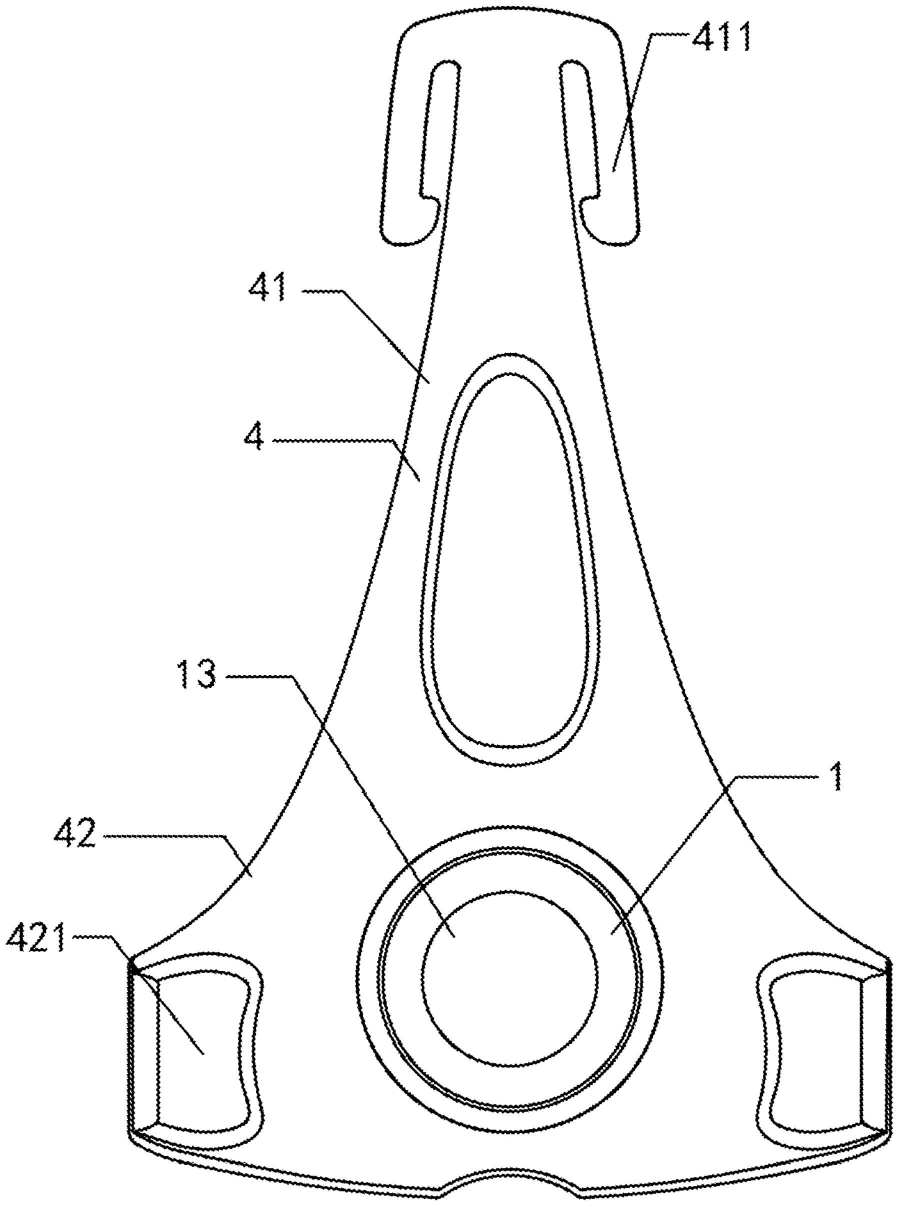
FIG. 1 is a schematic diagram of the connector and the frame in a connected state in accordance with an embodiment.

To make the purposes, features, and advantages of a connector for a frame of a respirator clearer and more understandable, the specific embodiments of this disclosure are detailed below, accompanied by illustrations. Many specific details are explained in the following descriptions to ensure a thorough understanding of the disclosure. However, the disclosure can be implemented in so many ways that are different from the ones described here, and professionals in the field can make modifications without departing from the spirit of the disclosure. Therefore, the disclosure is not limited to the specific embodiment disclosed below.

This disclosure introduces a modular connector that can be applied to frames and adapted for different face masks and elbows. The connector not only enhances the airtightness when the pressurized air flows through the elbow and face mask but also helps the patient feel comfortable during CPAP therapy and simplifies production. Additionally, to address the problems of exhaust and noise reduction in face mask assembly, the disclosure has made various improvements to this modular connector. These enhancements ensure that while fitting face masks and elbows of different models, structures, and functions, the connector also possesses exhaust and noise reduction capabilities, which guarantee smooth exhaust flow, reduce the complexity of setting up a noise reduction component, and make it easier for patients to clean components after use, which is crucial to prevent the long-term accumulation of moisture from breath, which could lead to mold and bacterial growth inside the tube, ensuring the device's cleanliness and patient safety. The structures of a connector for a frame of a respirator will be further elucidated through specific embodiments below.

Embodiment 1

This embodiment discloses a connector 1 for a frame of a respirator, as shown in various figures corresponding to this application, configured to connect to a face mask assembly and create a pathway for transmitting positive pressure air or breathable air, including a first interface end 11 for assembling with and communicating with a face mask 2, a second interface end 12 for assembling with and communicating with an elbow 3 (used to connect hoses and connector 1, delivering pressurized gas to the airway), and an annular passage 13 connecting the first interface end 11 and the second interface end 12, allowing positive pressure air to pass through and enter the airway. The axis of the connector 1 coincides with the axis of a gas outlet at the elbow 3. The gas outlet of the elbow 3, after receiving positive pressure air, from which the gas flows out and enters the connector 1, is the interface to the connector 1. The interface is the opening on the elbow 3 that connects the connection end of connectors. In other words, when both the connector 1 and the elbow 3 are of cylindrical structure, the gas outlet end of the elbow 3 is coaxial with connector 1, making the width of the gap at various places of the connecting part between the connector 1 and the elbow 3 the same, to avoid loosening at the connection between the connector 1 and the elbow 3. The connector 1 passes through the central opening 40 of the frame 4 and is fixedly connected to the frame 4 to prevent sliding or rotation of the connector 1 relative to the frame 4, preventing the elbow 3 and hose from swinging and interfering with the treatment or causing discomfort. The structure of the connector 1 also avoids the issue of loosening at the connection between the connector 1 and the frame 4 due to relative sliding, which could adversely lead to the connector 1 pulling the face mask 2, therefore causing the face mask 2 to fall off from the face. Thus, the connector 1 ensures the stability of the respiratory therapy. Furthermore, the connector 1 is configured to be fixed on the frame 4 and, together with the frame 4 and the headband, stabilizes to limit the face mask 2 on the face, thereby transferring the force of the headband to the face mask 2 to form a seal. The connector 1 connects the elbow 3 and the face mask 2, jointly constituting a non-invasive seal to deliver pressurized air from the ventilator to the airway, thereby achieving an anapestic effect. Specifically, the frame 4 is connected to the connector 1 to secure the face mask 2 and the frame 4 is constructed to have a continuous negative curvature surface with a C-shaped cross-section, complementing and conforming to the external contour of the face mask 2, and the shape of the frame 4 is also snug fit to the face mask 2, which allows the face mask 2 to comfortably form a sealed gas space on the face.

Figure 8:
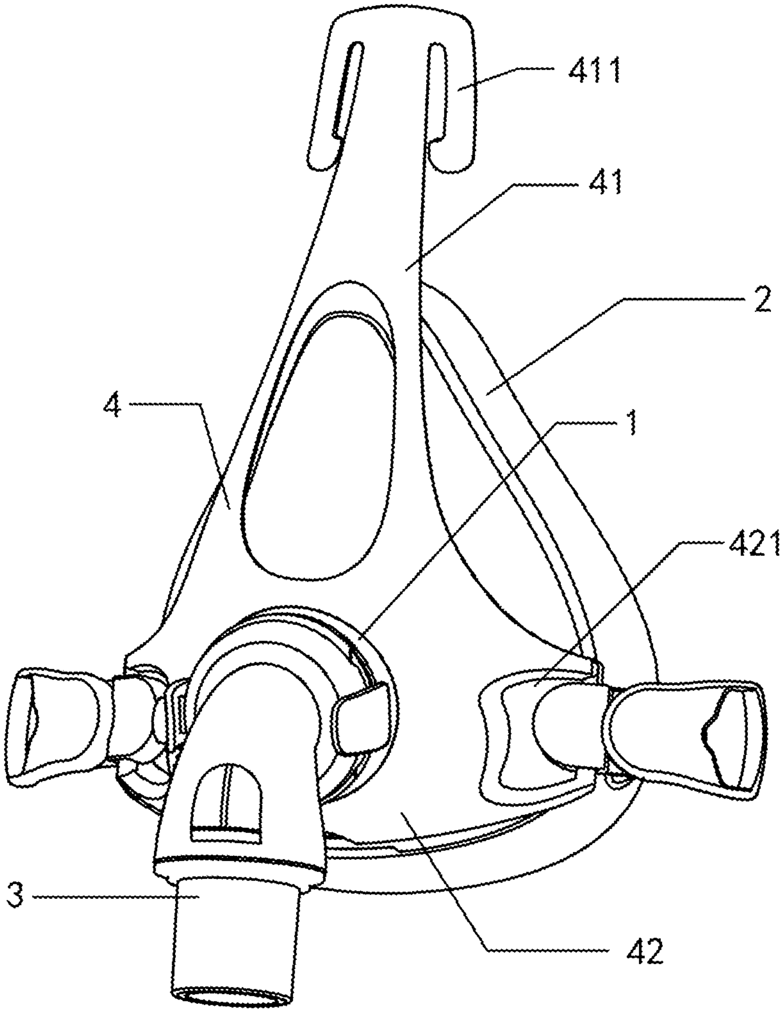
FIG. 8 is a schematic diagram showing the assembly of the connector, frame, elbow, and face mask in accordance with an embodiment.
Figure 9:
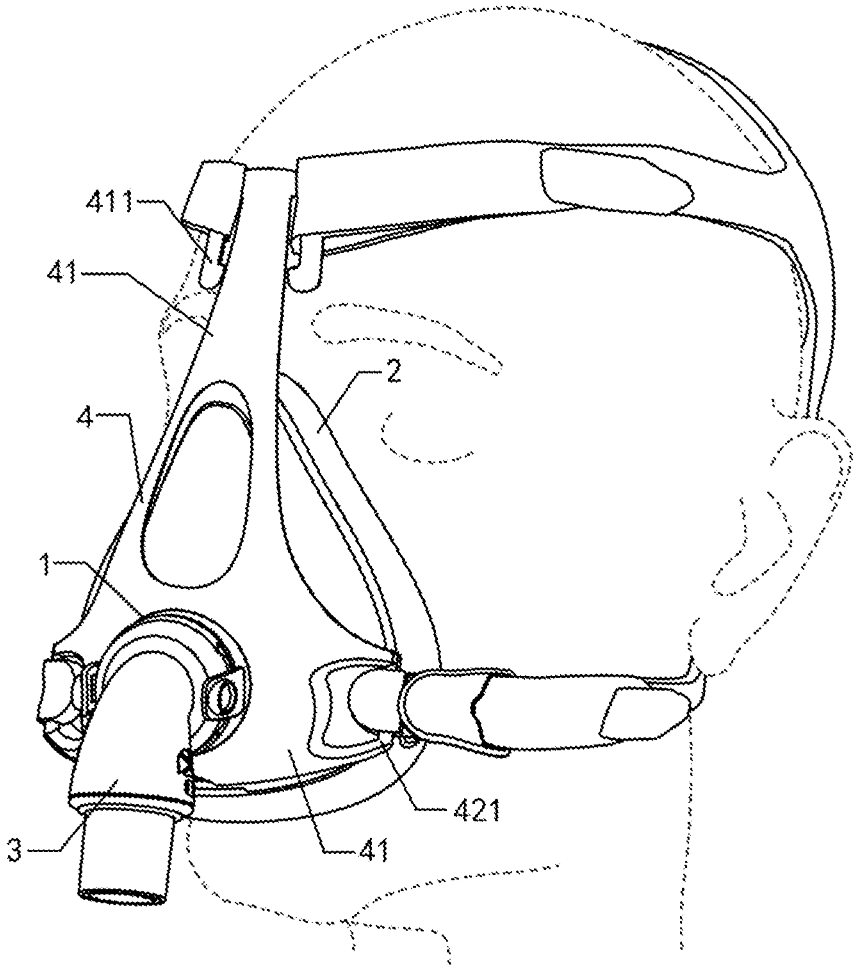
FIG. 9 is a schematic diagram showing a usage scenario of the connector, frame, elbow, and face mask in accordance with an embodiment.

In the embodiment, the frame 4 is made from rigid material or semi-rigid material. When the frame 4 is made from rigid material, the mechanical strength of the frame 4 is ensured to avoid the frame 4 being broken or damaged during use; When the frame 4 adopts semi-rigid material, it is convenient for the frame 4 to generate a small level of deformation during installation to adapt to the face, improve the fit degree of the frame 4 and the face and help the patient feel more comfortable when wearing the face mask 2 and the frame 4. As shown in FIG. 8 and FIG. 9. During use, by using the hook section 411 of the forehead support arm 41 on the frame 4 and the side arm connects opening 421 on both sides of arm 42, and by utilizing support straps, magnetic buckles, or releasable clips formed by flexible materials, the frame 4 and the connector 1 form an integral component to encircle the head and apply a certain pressure to the face mask 2 gradually, allowing the face mask 2 to conform to the face gradually. At least a portion of the frame 4 contacts the face of a patient; the frame 4 is configured in such a way that the frame 4 covers at least a portion of the face mask 2 when the frame 4 and the face mask 2 are connected.

At least part of the wall thickness of the connector is less than 3 mm, the length of the connector is at or between 3 to 50 mm. The outer periphery of the connecting part on the connector 1 and the frame 4 is smaller than the inner periphery of the central opening 40 of the frame 4. Thus, the connector 1 can smoothly pass through the central opening 40 of the frame 4 and be fixed with the frame 4, and when the connector 1 is connected to the frame 4, the outer side of the connector 1 is at least partially fitted to the inner side of the central opening 40 of the frame 4, thus providing a sealed passage for the pressurized air. Further, the overall length of the connector 1 is greater than the wall thickness at the central opening 40 of the frame 4; the maximum wall thickness of the frame 4 is not more than 2 mm. In other words, the length of the shortest part of the connector 1 is still greater than the wall thickness of the central opening 40 of the frame 4. Therefore, the connector 1 passes through the central opening 40 of the frame 4 and the condition provided for the adaptation of the connector 1 to the face mask 2 and the elbow 3 is satisfied, that is, the connector 1 can be connected to the face mask 2 and the elbow 3 after passing through the central opening 40 of the frame 4. Preferably, the wall thickness of each part of the connector 1 can be less than 2 mm, so that the overall weight of the connector 1 can be effectively controlled and the burden of the patient wearing the face mask assembly can be alleviated.

In the embodiment, the first interface end 11 is detachably connectable to the face mask 2, the second interface end 12 is detachably connectable to the elbow 3, and the connector 1 is connected to the elbow 3 and the face mask 2 to form a seal. The face mask assembly includes the connector 1, the frame 4, the face mask 2, and the elbow 3. The connector 1 and the frame 4 can be disassembled by a snap-fitting (corresponding grooves set on the frame 4 and corresponding bulges set on connector 1, and the connector 1 and the frame 4 can be connected by at least slight deformation of connector 1), the rotary fitting or magnetic attraction (connected by positive and negative magnets configured on the frame 4 and the connector 1, respectively). The non-integrated design facilitates the replacement of different combinations of the frame 4 and the connector 1, facilitates the quick release and disassembly of the frame 4 and other components on the face mask assembly for the patient, facilitates the modularity of the components of the frame assemblies and reduces the production cost of components and saves raw materials. The connector 1 and the face mask 2 are connected by a snap-fitting (a corresponding groove or projection is provided on the face mask 2, and therefore the connector 1 and the face mask 2 can be connected by at least slight deformation of connector 1), rotary fitting or magnetic attraction. The connector 1 and the elbow 3 are connected by a snap-fitting, a ball and socket rotation or a hinge connection, and the connector 1 and the elbow 3 may also be connected by magnetic attraction or clip (by pinching mechanical structure, the elbow 3 is released onto the interface of the frame 4). Both the face mask 2 and the elbow 3 form a releasable connection (detachable connection) on connector 1, which contributes to the reliability of the seal, extends the service life of the product and protects the environment. The design to ensure that the sealing structure is designed into a single component is not only an improvement of its own sealing performance, but also a simplification of the structure and the production process. Connector 1 is connected to the frame 4 through the central opening 40 of the frame 4 to allow the pressurized air to pass through the elbow, forming a relatively sealed pathway between the connector 1 and the face mask 2 to the airway leading to the patient. The patient may have different choices for the different connection methods, so the connector 1 can be set in the frame 4 in different connection methods to increase the variety of combinations for the patient and to provide a greater range of choices.

Figure 10:
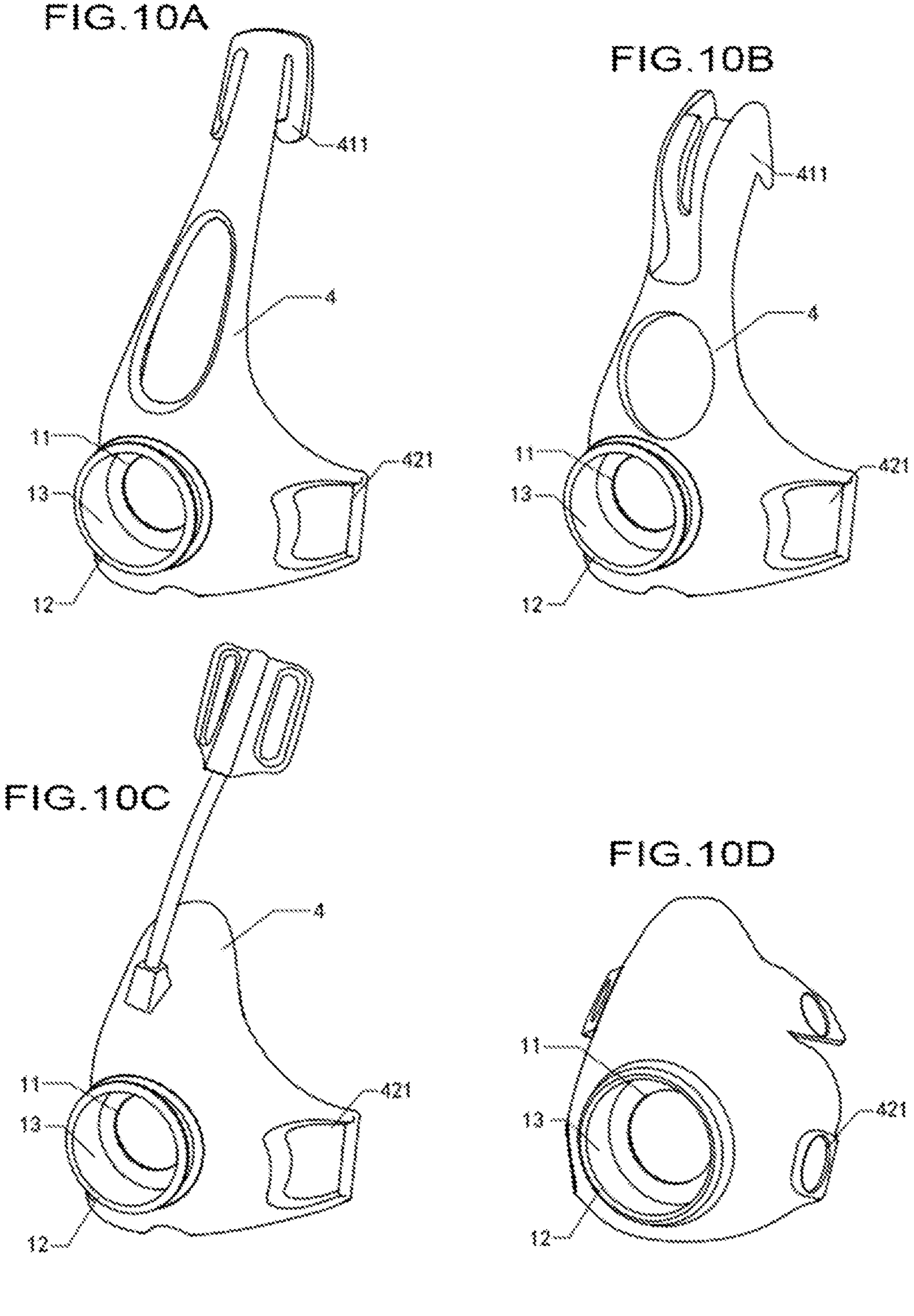
FIG. 10A, FIG. 10B, FIG. 10C and FIG. 10D are schematic diagrams showing how the connector connects with several different types of frame structures in accordance with an embodiment.

According to different usage scenarios, connector 1 can be adapted with different types of frames 4, see, e.g., FIG. 10. The embodiment shows the connector 1 connecting with different types of frames 4, as opposed to elbows 3 and face masks 2, a variety of frames available on the market also provide patients with different choices. The detachable feature between the connector 1 and the frames 4 determines that a variety of connector 1 not only can be adapted with different the elbow 3 and the face mask 2, but also can be selected to combine different types of frames 4 to form a whole new frame assemblies according to different interface types. The diversity and flexibility of the design make it more convenient and more simplified for patients to choose their face mask assembly. In addition, connector 1 may be fixed to the frame 4, by using a variety of different connection methods. See, e.g., FIG. 7. FIG. 7 shows the different connection methods of the connector 1 and the frame 4. The connector 1 and the frame 4 may be connected in a variety of ways such as a snap-fitting (as shown in FIG. 7A), a plug (as shown in FIG. 7B), a ball and socket rotation (as shown in FIG. 7C), etc., which are not necessarily limited to the single connection method described above, but may also be assembled using two or more of the above connection methods.

Figure 4:
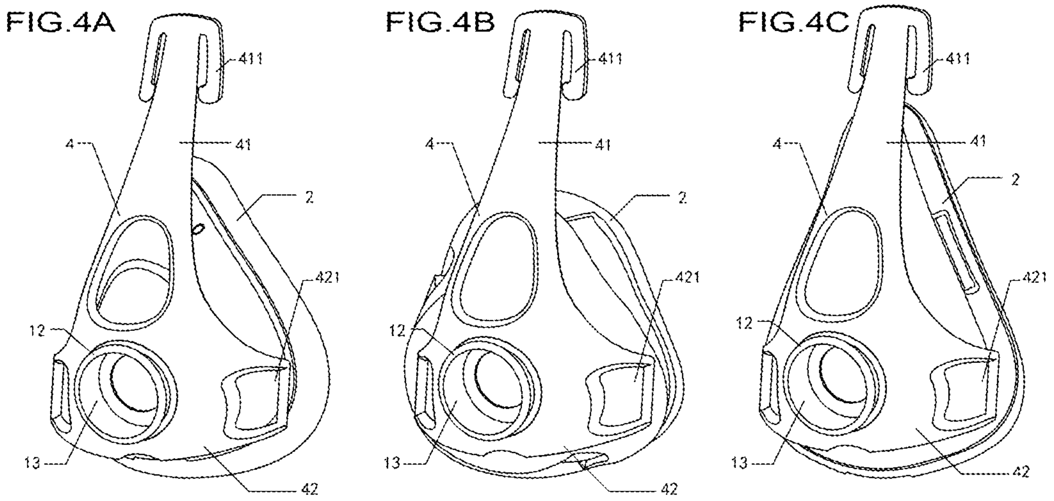
FIG. 4A, FIG. 4B and FIG. 4C are schematic diagrams showing the connector used on different designs of face masks in accordance with an embodiment.
Figure 20:
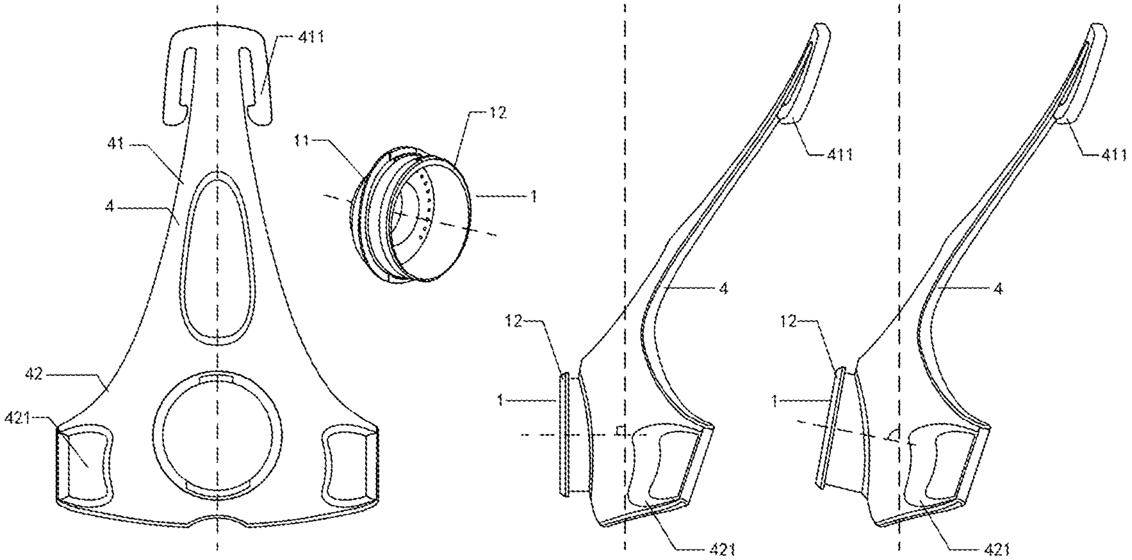
FIG. 20 is a schematic diagram showing the angle between the central axis of the connector and the symmetrical axis of the frame in accordance with another embodiment.

The connector 1 can be matched with a variety of different styles of face masks 2. See, e.g., FIG. 4. The embodiment shows the way connector 1 combined with the frame 4 matches the different types of the face mask 2. In the existing market, the face mask 2 produced by different manufacturers and the face mask 2 in different models are different and the combinations of the frame 4 and the face mask 2 are not the same either, so there is a phenomenon that different models of the frame 4 and the different models of the face masks 2 cannot be combined. In the embodiment, connector 1 that can be detachable to the frame 4 can adapt to different face masks 2 only by replacing different connectors 1, so that the connector 1 can be combined with the frame 4 to connect different models or different interfaces of the face mask 2, which can provide patients with more choices with respect to the face masks 2, so that the patient can select all face masks 2 on the market according to his or her own needs and preferences and the range of choice for face mask assemblies is also enlarged. Connector 1 and the frame 4 are connected to the face mask 2 via the first interface end 11, and a straight line formed by the center of the first interface end 11 of the connector 1 and the central opening 40 of the frame 4 defines the central axis of the air inlet of the face mask 2. In order to ensure the comfortability of matching with other components after the connector 1 is fixed with the frame, in this embodiment, a central axis of the connector 1 is configured to make an angle at or between 10° to 90° with the axis of symmetry of the frame 4, as shown in FIG. 20, and more preferably, the angle can be at or between 35° to 90° to accommodate different ventilator placement positions as well as to accommodate different postures of the patient. In another embodiment, connector 1 may also be configured to be secured to the face mask 2 and the central opening 40 on the frame 4 by means including, but not limited to, swivel fastening, gluing and welding.

Figure 5:
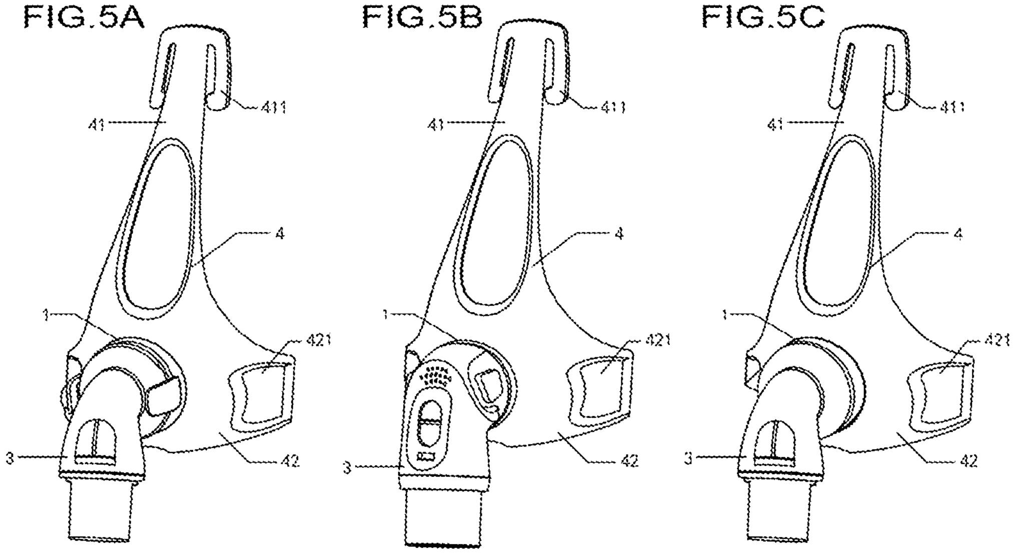
FIG. 5A, FIG. 5B and FIG. 5C are schematic diagrams showing the connector used with different styles of elbows in accordance with an embodiment.

The connector 1 can be used with a variety of styles of the elbow 3. See, e.g., FIG. 5. The embodiment shows the way connector 1 matches three different forms of elbows 3, clip (as shown in FIG. 5A), pinch (as shown in FIG. 5B), and ball and socket (as shown in FIG. 5C). When different connectors 1 are connected to the frame 4, it means that the frame 4 has different forms of interfaces to connect with the elbows 3. Existing elbows 3 on the market, such as clip/pinch/ball-and-socket type elbows, can correspond to modular connector 1 with corresponding types of interfaces, and modular frame 4 with corresponding types of interfaces can be connected to different types of elbows 3. Therefore, the user can flexibly choose the match connected by the elbow 3 and the face mask 2 with the frame 4, which provides more ways of matching for the user.

Figure 6:
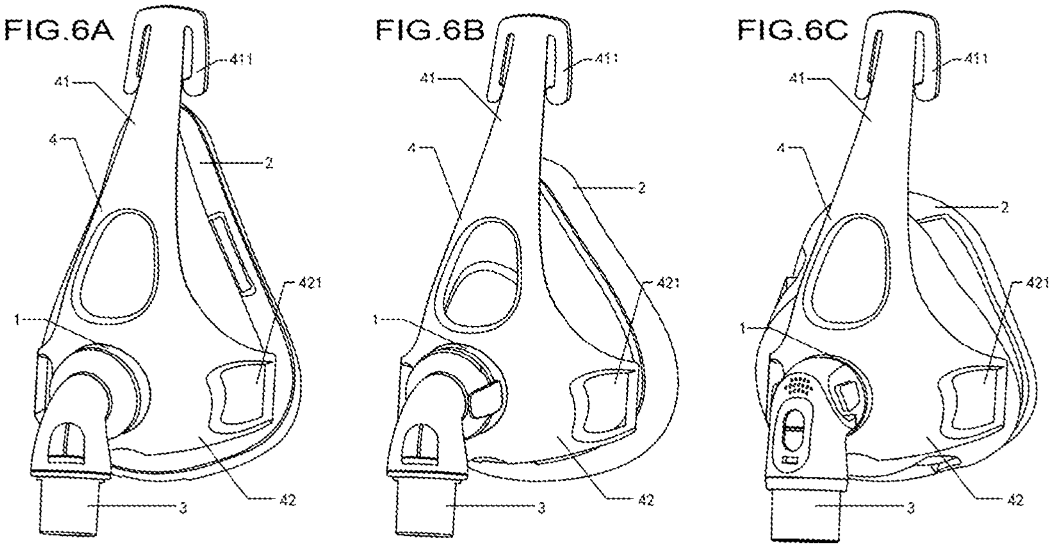
FIG. 6A, FIG. 6B and FIG. 6C are schematic diagrams showing the connector used with different styles of face masks and elbows in accordance with an embodiment.

The connector 1 can be used with a variety of different styles of the face mask 2 and the elbow 3 at the same time. See, e.g., FIG. 13. The embodiment shows how different connectors 1 and frames 4 form different frame interfaces (FIG. 13A shows a straight-tube interface, and FIG. 13B shows a ball-and-socket interface). As the elbow 3 and the respiratory face mask 2 are all combined with the connector 1 through the openings on both ends of connector 1 and then connected to the frame 4, the connection between the frame 4 and mask 2, as well as the elbow 3, is manifested at connector 1. That connector 1 and the frame 4 are independent of each other to ensure that the frame 4 and the face mask 2 and elbows 3 can be combined and are adaptive to each other. Replacing only connector 1 without replacing the entire frame assembly in order to adapt to the shape of mask 2 and the elbow 3 saves on raw materials and production costs. The design also makes it easy to maintain the frame 4, so that the whole product is more controllable, flexible, efficient and reliable. The connector 1 can be used with a variety of different styles of frames 4, please refer to FIG. 6 for the specifics. The embodiment demonstrates that by replacing different connectors 1 and combining them with the same frame 4, the frame assemblies with different interfaces are formed. These different interfaces of the frame assemblies can correspond to different elbows 3 and face masks 2. As a result, the frame 4 can not only connect different face mask 2 with specified elbows 3 but also connect different elbows 3 with specified face masks 2. Moreover, the frame assemblies allow for the flexible combination of different elbows 3 and face masks 2. For example, a face mask 2 from Brand A with an elbow 3 from Brand B may be used, enabling the arbitrary combination of elbows 3 and face masks 2 from different brands. The disclosure eliminates the need for manufacturers to develop specific connectors for the compatibility of face masks 2 and elbows 3, which has a positive impact on the design and development of the product.

The above-mentioned connectors offer at least the following beneficial effects:

1. Compatibility with different face masks, low product development costs, shortened development cycles, and material savings: The modular design involves the independent production of connectors and frames, which are then assembled, allowing for the separation of frame assemblies from the mask and elbow. This modularity of connectors enables patients to adapt to different situations by simply replacing different types of intermediate connectors to help the frame assemblies adapt to different types of face masks or elbows. In the market, there are various types of face masks and elbows, but not all of face masks and elbows can be adaptively connected to the frame. Therefore, the aforementioned connectors have been designed and introduced. After both the frame and connectors are independently molded, they can be connected in the later stages. Once different connectors are attached to the frame, it can accommodate not only Brand A's face mask but also Brand B's face mask or other various brands. The connectors are used to connect the face mask and the elbow, ensuring that the connection of the face mask, elbow, and frame is fixed using the connectors only. By changing different connectors, the frame can be adapted to connect different types of elbows and face masks. The modular design of the connector allows the connectors to form independent modules relative to various parts of the product, which can be individually designed, developed, tested, and maintained. The modular design of the connector makes modifications and replacements straightforward, as they only require changing the corresponding connector module without affecting the entire face mask assembly, which saves on materials and production costs, facilitates product maintenance, shortens product development time and manufacturing cycles, and makes it easier to improve product quality and adapt to rapid market changes.
2. Easy maintenance: The separate connector mold design also reduces the complexity of the face mask assembly, making the entire face mask assembly more manageable for patients. The entire face mask assembly is divided into several separate modules, making it easier to isolate and resolve issues when a module from the face mask assembly encounters a problem, which helps to reduce the risk of failures and minimizes the impact during replacements, thereby protecting the environment by reducing carbon emissions and conserving resources. It achieves a green and sustainable design.
3. The connectors with elbows of different functions and structures may be combined: Different patients have their own needs for noise reduction or non-noise reduction. Some patients also have specific requirements for airflow pressure due to their individual conditions. Therefore, patients need to choose elbow connectors with different features, including noise reduction or non-noise reduction, varying numbers of holes, hole sizes, and even shapes. A small portion of patients with respiratory insufficiency and respiratory failure may require ventilation assistance and may need to choose elbow connectors without holes. Typically, elbows with different functions have different types of connection structures, such as ball-and-socket types, left-right rotation types, and a snap-fitting. There are also different interfaces of elbows with various angles and lengths, some of which are not compatible with frames. Since there is currently no frame on the market that is compatible with several different types of elbows, this disclosure separates the assembly of a frame and a connector. This split connection structure design provides a new possibility for patients who want to use a frame but do not match the elbow in the assembly, so the frames can adapt to various elbows by changing the connector, giving patients a different feeling about the use of the mask and elbow in conjunction with the frame assemblies.
4. Low manufacturing cost: In the original design, the frame and connector were integrated, with the frame connecting to the elbow and the face mask through a snap-fitting that corresponds to the grooves and protrusions in the respective structures. Additionally, the frame itself has a complex curvature that needs to match the face mask, which makes the structure more complex and increases the difficulty of molding and, subsequently, the cost of mold manufacturing. The design of separating the frame from the connector simplifies the structure, making mold manufacturing easier and reducing the associated manufacturing costs, which, in turn, reduces the production cycle, saving the cost and shortening the development cycle in the development process.
5. Easy to clean: The modular design of the connector also provides a more user-friendly way to maintain patient hygiene. When the connector is securely fixed to the frame and cannot be detached, the overall structure formed by the frame and the connector is more complex, making it susceptible to bacterial growth due to inadequate cleaning, thereby posing a threat to the patient's health. The disclosure attaches the connector to the frame, forming a modular connector. With this design, when patients perform cleaning, the detachable structure, as opposed to the complex structure of the entire component, allows for cleaner and simpler cleaning, reducing the probability of bacterial growth and safeguarding the patient's health.

Embodiment 2

The disclosure discloses a connector 1 for a frame of a respirator, configured to connect to a face mask 2 assembly and create a pathway for transmitting positive pressure air or breathable air, including a first interface end 11 for assembling with and communicating with a face mask 2, a second interface end 12 for assembling with and communicating with an elbow 3, and an annular passage 13 connecting the first interface end 11 and the second interface end 12, allowing pressurized air to pass through and enter the airway. The axis of the connector 1 coincides with the axis of an gas outlet at the elbow 3, with the connector 1 passing through the central opening 40 of the frame 4 and being securely connected to the frame 4 to prevent sliding or rotation of the connector relative to the frame 4. The length of the connector 1 is at or between 3 to 50 mm; the inner diameter of the connector 1 does not exceed 80 mm; and the minimum ratio between the opening area of the second interface end 12 and the outer surface area of the frame 4 is 1:20.

Compared to Embodiment 1, this embodiment specifies the inner diameter of connector 1 and the ratio of the opening area of the second interface end 12 to the outer surface area of the frame 4. The diameter of the inner edge near the face mask 2 on the connector 1 (the inner diameter of the first interface end 11) determines the pressure of the gas entering the face mask 2. To prevent difficulties in inhalation due to excessively low gas pressure and to avoid installation issues caused by an excessively large or small opening size at the second interface end 12 of connector 1. Furthermore, the inner diameter of connector 1 is not greater than 80 mm, and the minimum ratio between the opening area of the second interface end 12 and the outer surface area of the frame 4 is set at 1:20.

Figure 2:
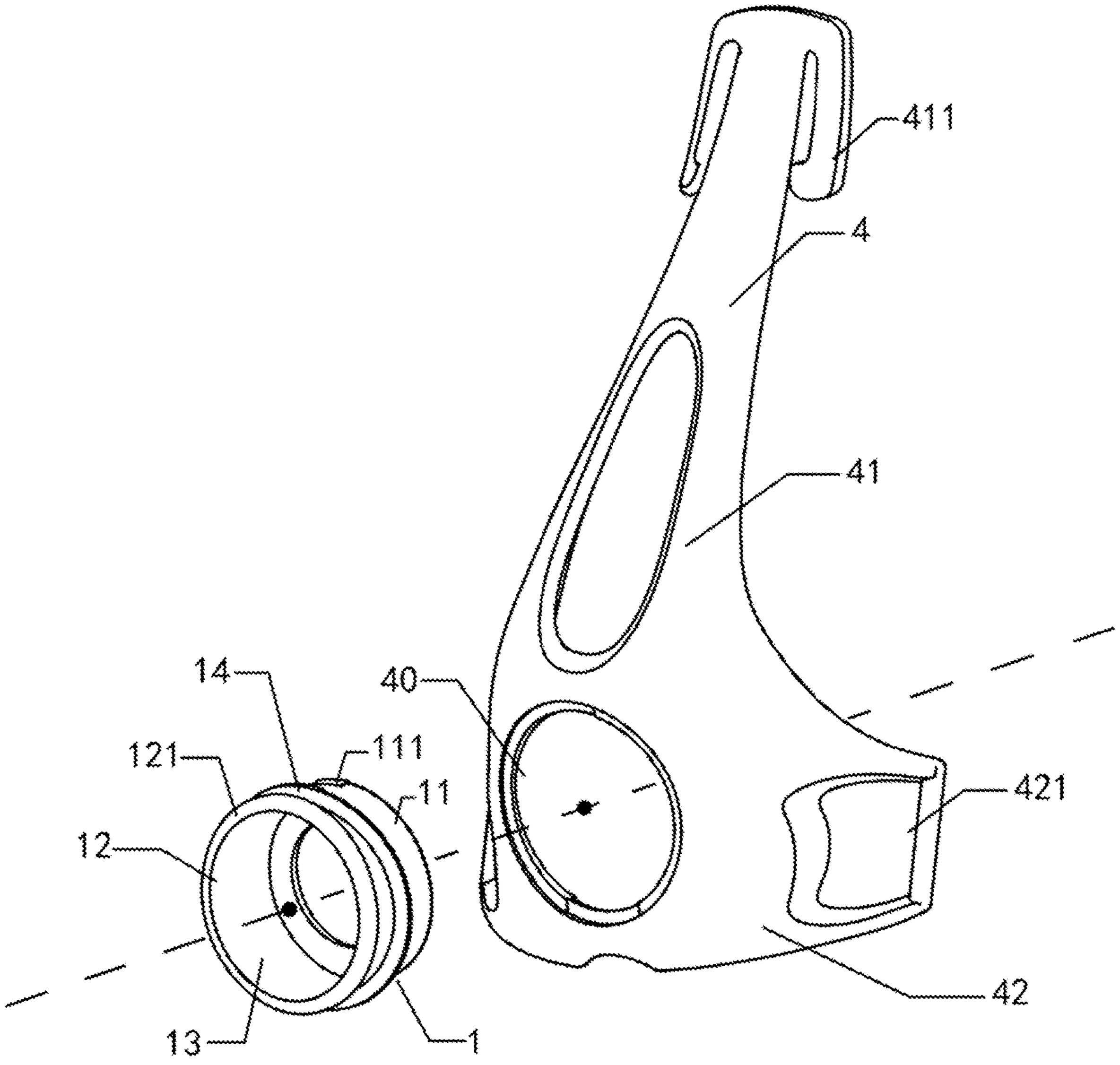
FIG. 2 shows an exploded schematic diagram of the connector and the frame in accordance with an another embodiment.
Figure 11:
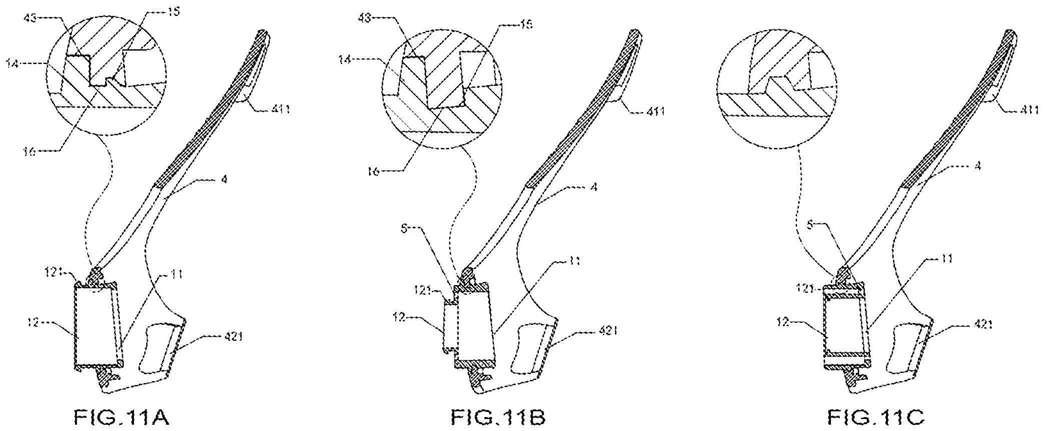
FIG. 11A, FIG. 11B and FIG. 11C are cross-sectional schematic diagrams of the connector and the frame connection in accordance with another embodiment.

In the embodiment, the central opening 40 of connector 1 and the frame 4 are secured together using a snap-fit mechanism. See, e.g., FIGS. 2, FIG. 3, and FIG. 11. Connector 1 includes a gasket 14 located between the first interface end 11 and the second interface end 12. On the side of the frame 4 facing the second interface end 12 of connector 1, there is an indentation 43 along the edge of the central opening 40 of the frame 4.

The gasket 14 is embedded into this indentation 43 when connector 1 is assembled with the frame 4. The indentation 43 can be seen as a recessed groove located within the central opening 40 of the frame 4. The purpose of indentation 43 is to engage with the protruding part, which is the gasket 14, used to position, stabilize, and enhance the force of the closely connecting connector 1 in adjacent sections. In the embodiment, the gasket 14 has at least one protruding feature. The gasket 14 is configured to position the frame 4 relative to connector 1, limiting the installation position of connector 1 on the frame 4. The gasket 14 corresponds to and fits within the sunken indentation 43 along the inner wall of the central opening 40 of the frame 4. To ensure a tight fit and proper positioning of the frame 4 with connector 1, the gasket 14 conforms to the curvature of the frame 4, presenting a non-flat ring that gradually shifts from the central portion towards the sides, eventually offsetting towards the second interface end 12. When connector 1 is connected to the frame 4, the gasket 14 is accommodated within the indentation 43 of the frame 4, and it exposes towards the front side of the frame 4.

The connection method between connector 1 and the face mask 2 is a snap-fit connection. See, e.g., FIG. 3 and FIG. 12. The embodiment demonstrates that connector 1 is connected to the face mask 2 using protrusions or recesses (FIG. 12A shows a protrusion form and FIG. 12B shows a recess form). Connector 1 is separate from the frame 4. The connection between connector 1 and the frame 4 can take the form of protrusions integrated into a single unit on the two ends and middle of connector 1, which engage with corresponding recesses on the central opening wall of the frame 4. Alternatively, the connector 1 can have grooves at its ends and middle to interlock with protrusions on the central opening wall of the frame 4, forming a snap-fit connection. Moreover, the connection between the connector 1 and the frame 4 can also be achieved through other methods such as adhesive bonding, ensuring a stable and immovable fixed connection between the connector 1 and the frame 4.

Furthermore, the outer surface of the first interface end 11 includes a first protrusion 111, and the outer surface of the second interface end 12 includes a second protrusion 121. Between the first protrusion 111 and the gasket 14, there is a positioning protrusion 15. Between the positioning protrusion 15 and the gasket 14, a positioning groove 16 is formed, which matches the inner edge of the central opening 40 of the frame 4. Additionally, at least one side of the positioning protrusion 15, which is near the second interface end 12 or is far away from the second interface end 12, is sloped.

In the embodiment, both the first protrusion 111 and the second protrusion 121 are integrally molded with the connector 1. The connector 1 forms a releasable connection on both sides of the elbow 3 through the first protrusion 111 and a releasable connection with both sides of the elbow 3 through the second protrusion 121. The first protrusion 111 is used to attach to the face mask 2 and has a smooth surface curvature. To ensure that the connection between the connector 1 and the elbow 3 does not come loose, leak, or become unstable during use, and to simplify the disassembly and wearing process for patients, the connection between the connector 1 and the elbow 3 is designed as a simple mechanical connection. The meshing and engagement between the connector 1 and the elbow 3 provide a good level of tightness and stability. Users can choose the appropriate connection method of the connector 1 and the elbow 3 based on their needs to ensure the proper operation of the medical equipment and enhance the user experience. Additionally, at the central opening 40 of the frame 4, there are one or more interlocking interfaces that mate with the second protrusion 121 to form a sealed connection, which facilitates quick disassembly of the frame components and the face mask 2 for multiple wearing configurations, improving user comfort and convenience. In one embodiment, e.g., FIG. 3, the connector 1 can take various forms based on structural differences in the components it interfaces with. The first protrusion 111 on the connector 1 can be positioned at some distance away from the end face of the first interface end 11 (as shown on FIG. 3B), or the first protrusion 111 on connector can be positioned so that the end face of the first protrusion 111 is flush with the end face of the first interface end 11 (as shown on FIG. 3A). In other situations, the first protrusion 111 can be omitted as needed.

Embodiment 3

In the disclosure, a connector 1 for a frame of a respirator is provided, configured to connect to a face mask assembly and create a pathway for transmitting positive pressure air or breathable air. The connector, configured for a removable attachment to a frame in a face mask assembly by insertion or surface contact, includes a first interface end 11 for assembling with and communicating with a face mask 2, a second interface end 12 for assembling with and communicating with an elbow 3, and an exhaust port 5 that permeates an inner surface of the connector 1 and an outer surface of the connector 1, communicating with an external environment to allow internal gas to flow out. An outer periphery of a section in which the connector 1 fits with the frame is smaller than an inner periphery of a central opening 40 of the frame 4 configured to accommodate the connector. The exhaust port 5 has at least one of the following characteristics:

there is at least one exhaust port 5;

diameters of two ends of one exhaust port 5 are different; and a total area of the exhaust port 5 accounts for at or between 3% to 90% of an external surface area of the connector 1.

In comparison to Embodiment 1 and Embodiment 2, an exhaust port 5 is added on the connector 1 in Embodiment 3. The addition of an exhaust port 5 on the connector 1 and allowing the frame to be adaptable to different face masks and elbows provides users with more options while ensuring effective exhaust. Through innovative connection methods, adaptability design, and simultaneous optimization of performance, the compatibility, convenience, and comfort of wearing therapeutic devices are enhanced, further promoting patient compliance with treatment. The exhaust port 5 forms a channel connecting the sleep apnea treatment device and the external environment, maintaining the patient's ventilation effectiveness and preventing the accumulation of carbon dioxide inside the face mask assembly. Additionally, the exhaust port 5 can reduce the noise of internal airflow, reducing discomfort for users when using the face mask assembly.

In the embodiment, see, e.g., FIGS. 14A, 14B, FIGS. 16A-16C, and FIGS. 17A-17C, positive pressure air is delivered to the upper airway through a combination between the connector 1 and the face mask, frame, elbow, and other components. Simultaneously, the exhaled waste gas can be discharged through the exhaust port 5 on the connector 1.

In the embodiment, the number of the exhaust port 5 is set to be at least one, providing a flow pathway for exhaled gas on the connector 1. The diameters at both ends of the exhaust port 5 are different. Ideally, the inner diameter of the exhaust port 5 near the face mask end is greater than the inner diameter of the exhaust port 5 near the elbow end. In other words, the exhaust port 5 has a conical structure, which allows exhaled gases to be expelled with less resistance due to the pressurizing effect of the conical structure, making exhalation easier for the patient. The total area of the exhaust port 5 is set to occupy at or between 3% to 90% of the outer surface of the connector 1, which ensures that connector 1 has a sufficient exhaust area, preventing patients from experiencing asphyxiation in certain situations. In one embodiment, when there is more than one exhaust port 5, these ports are distributed evenly or unevenly along the annular passage 13 of the connector 1, which allows exhaled gas to be expelled from multiple locations along the circumferential side of the connector 1, further reducing the burden on patients during exhalation. In one embodiment, the exhaust port 5 can also be arranged randomly on the connector 1.

Figures 14A, 14B:
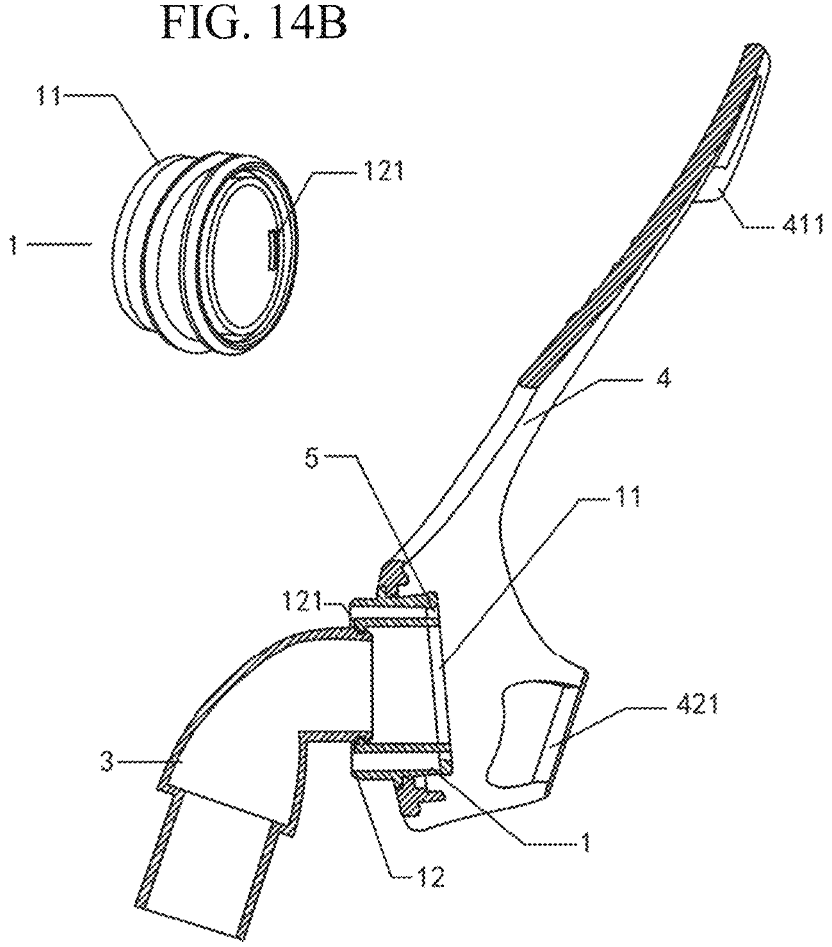
FIG. 14A and FIG. 14B are a three-dimensional schematic diagrams of the connector and a cross-sectional view of the assembled connector, frame, and elbow in accordance with another embodiment.

In the embodiment, the outer periphery of the second interface end 12 is smaller than the outer periphery of the first interface end 11. In other words, the aperture on the connector 1 that adapts to the elbow 3 at one end is smaller than the aperture on the connector 1 that adapts to the mask 2 at the other end, which aims to provide the patient with a larger channel for respiratory gases, reducing the difficulty of inhalation during respiratory therapy. In the embodiment, the connector 1 forms a releasable connection with both sides of the elbow 3 via the second protrusion 121. On the side near the second interface end 12 of the gasket 14, a step or inclined plane is formed with the second interface end, and the exhaust port 5 is set on this step or inclined plane, penetrating the inner and outer surfaces of the connector 1. In another embodiment, the outer periphery of the second interface end 12 of the connector 1 is greater than the outer periphery of the first interface end 11. In another embodiment, connector 1 has a double-layered wall, as shown in FIG. 14B. The exhaust port 5 is set on a surface forming a certain angle with the inner and outer walls and the surface is used to connect the inner and outer walls. In this situation, the second protrusion 121 is set on the inner layer wall of the connector 1.

In one embodiment, an angle between an axis of the exhaust port 5 and an axis of the connector 1 is at or between 0° to 90°. By adjusting the angle between the axis direction of the exhaust port 5 and the axis direction of the connector 1, airflow can be guided to discharge from a specific direction to meet the different exhaust needs of the patient. Additionally, in the embodiment, the exhaust port 5 can have a circular, elliptical, semi-circular, or square structure, or it can have other non-standard shapes. See, e.g., FIGS. 16A-16C and FIGS. 17A-17C; the embodiment illustrates different forms of the exhaust port 5. The different forms of the exhaust port 5 can affect the flow method, velocity, and uniformity of the exhaust air. Therefore, the shape of exhaust port 5 can be arranged differently and designed in different paths and shapes based on user needs and functionality. For example, for the shape of the exhaust port 5, a linear exhaust groove can guide the airflow to discharge in a specific direction, and adjusting the angle of the exhaust port 5 can improve the airflow direction, reducing external interference. The size, number, and layout of the exhaust port 5, etc., also play a role in affecting the exhaust airflow. Through reasonable design and layout, optimal exhaust performance can be achieved, thereby enhancing the performance of the treatment equipment and the user experience. The shape of the exhaust port 5 can be selected based on its design path, set angle, and manufacturing requirements, which are not reiterated here.

When the form of exhaust port 5 is in the shape of a hole, the part used on the connector 1 to create exhaust port 5 is the exhaust hole. At the same time, the total area of exhaust port 5 occupies at or between 3% to 50% of the inner and outer surface areas of the connector 1. The exhaust holes are placed on the connector 1, and the shapes of the exhaust holes include but are not limited to circular, elliptical, semi-circular, and square shapes.

The connector for the frame of a respirator in the embodiment can achieve at least the following technical benefits:

1. By separating the exhaust port from the mask or elbow, a modular assembly is created, and can be replaced individually. Separately molding and then securely installing the connector onto the mask frame solves the problem of needing to replace the entire exhaust assembly for different patients with varying exhaust needs. The modular design of the connector allows patients to focus on specific connectors rather than the entire respiratory component system, enabling quick replacements and rapid adaptation to emerging masks or elbows on the market, thus enhancing the connector's usability and reliability. The modular design of the connector also reduces patient disposal rates on respiratory components, gradually decreases carbon emissions globally, making it more environmentally friendly. Additionally, the design of attachable connector saves patients a significant amount of time and cost, as well as saving research and development personnel time and actual costs.

2. By replacing different connectors, it is possible for patients to use the connector to adapt different elbows and masks, meaning that the same elbow can be adapted to different corresponding masks through different connectors, or the same mask can be adapted to different elbows through different connectors. The modular design of connector allows for the reuse of identical components in different project configurations, thus, when connectors are fixed to elbows or masks, the design of the connector helps to avoid the need for repetitive development of same components in mask assemblies. The modular design of the connector utilizes existing modules to construct a more flexible face mask assembly, integrating multiple functions into small modular components, which ultimately saves development time and resources. Further, the reliability of existing masks and elbows has been tested and proven through usage. Developing a detachable connector for exhaust avoids the trial and error costs of integrating exhaust design into new masks or elbows, which, in turn, enhances development efficiency and quality. Once a connector for exhaust is in use, maintaining and upgrading a standalone modular assembly is easier and more cost-effective than maintaining an entire face mask assembly with elbows or masks. Therefore, modular connector design also reduces the difficulty and cost of maintenance, bringing substantial economic benefits to the development process.

3. The diversity of elbows, masks, and frames on the market does not always allow for compatibility between different elbows, masks and frames. The single mode of compatibility restricts patients' choices when it comes to respiratory components. Patients have different needs and preferences when it comes to selecting components, and modular exhaust assemblies offer better connections between components, allowing users to autonomously choose respiratory components based on their needs and preferences, meaning that patients don't have to adhere to specific interface requirements, as modular connectors enable components with different interfaces to work together. The flexibility of changing modular components freely has a positive impact on both the market and users. Users can independently select the components they need from different manufacturers to match different modular assemblies. The flexibility provided by using modular respiratory components benefits both the market by maintaining the manufacturer's competitiveness and patients by providing more satisfactory solutions for a face mask assembly.

4. The modular connector design also offers a more user-friendly approach to cleaning for patients. When the exhaust port is integrated into the elbow or mask, the overall structure tends to be more complex, tending to prevent patients from making it clean, which can lead to the growth of bacteria and pose a threat to patients' health. By attaching the exhaust port to a separate connector, when it comes to cleaning, the modular structures do not have complex structures relative to the intergrated structures, which simplifies the cleaning process, making it more thorough and reducing the likelihood of bacterial growth, thus safeguarding patients' health.

Embodiment 4

As shown in FIGS. 15A-15D and FIGS. 18A-18D, in the disclosure, a connector 1 for a frame of a respirator is provided, configured to connect to a face mask assembly and create a pathway for transmitting positive pressure air or breathable air. The connector 1, configured for a removable attachment to a frame in a face mask assembly by insertion or surface contact, includes a first interface end 11 for assembling with and communicating with a face mask 2, a second interface end 12 for assembling with and communicating with an elbow 3, and an exhaust port 5 that permeates an inner surface of the connector 1 and an outer surface of the connector 1, communicating with an external environment to allow internal gas to flow out. The exhaust port 5 is distributed along the annular passage of the connector 1. An outer surface of the connector 1 includes noise reduction components 6, which include noise reduction materials set for corresponding exhaust port 5, with the noise reduction materials having at least one of the following characteristics:

a density of the noise reduction material is at or between 0.8 to 1.8 g/cm$^3$;

a surface area of the noise reduction material occupies at or between 3% to 90% of an outer surface area of the connector;

a thickness of the noise reduction material is at or between 0.1 to 0.5 mm; and a weight range for noise reduction materials is at or between 0.02 to 0.2 grams.

The connector 1 in this embodiment shares a similar structure and material with Embodiment 1. However, in comparison to Embodiment 1, Embodiment 4 includes the addition of an exhaust port 5. In the embodiment, unlike Embodiment 5, it incorporates a noise reduction component 6 at the exhaust port 5. The noise reduction component 6 reduces the noise generated due to the disturbance of gases expelled through the exhaust port 5. The addition of a noise reduction component 6 provides the connector 1 with additional noise reduction capabilities. Because different patients have varying tolerances for noise, the inclusion of the external noise reduction component 6 can improve user comfort and overall user experience. The noise reduction component 6 provides a quieter sleeping environment for patients. Users can choose to install or not install the noise reduction component 6 based on their needs, or they can switch between connectors 1 with and without the noise reduction component 6. Users can choose to install or not install noise-reduction component 6, or replace the connector 1 with or without noise-reduction component 6, based on their needs, providing an efficient, flexible, and reliable design. Moreover, placing the noise reduction component 6 at the exhaust port 5 of the connector 1 allows patients to choose to replace the noise reduction component 6 to extend the face mask assembly's lifespan. Adding the noise reduction component 6 to the connector 1 makes it relatively easy to replace or modify, and components that need to be modified are small in size, with an impact on minimal range, and there is no need for large-scale replacements or updates for the components in a face mask assembly. By replacing the noise reduction component 6 on connector 1, users can substitute for replacing the entire exhaust assembly that has noise-reduction materials, therefore extend the lifespan of other components, thus prolonging the presence of components on the face mask assembly in the market and reducing resource consumption caused by frequent discards of components on a face mask assembly.

In the embodiment, by specifying the density, weight, thickness, and surface area of the noise reduction material, the impact of the noise reduction component 6 on the connector 1 can be minimized, thus reducing the burden on patients wearing respiratory masks. In the embodiment, the noise reduction material is in the form of a mesh-like structure or a cotton fluff structure. The noise reduction material is made from materials such as cotton, nylon, or natural fabrics.

Figure 15E:
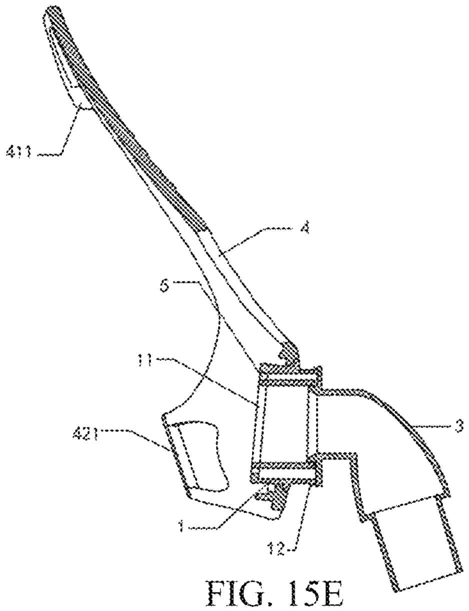
FIG. 15A, FIG. 15B, FIG. 15C and FIG. 15D are three-dimensional schematic diagrams of the connector and are cross-sectional views of the assembled connector, frame, and elbow in accordance with another embodiment.
Figure 15A:
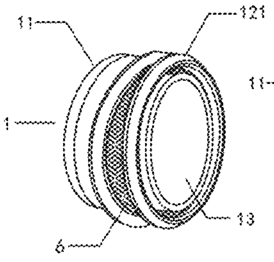
Figure 15B:
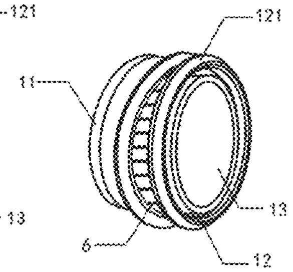
Figure 15C:
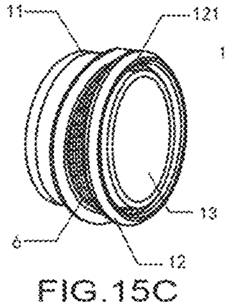
Figure 15D:
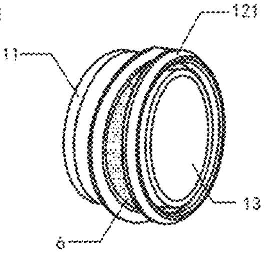
Figure 16A:
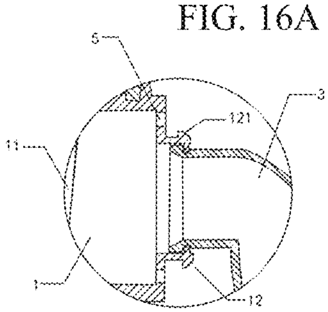
FIGS. 16A, 16B, and 16C are each a three-dimensional schematic diagram of another version of the connector and a cross-sectional view after the connector assemble with the elbow in accordance with another embodiment.
Figure 16B:
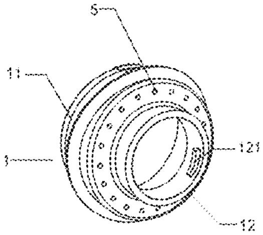
Figure 16C:
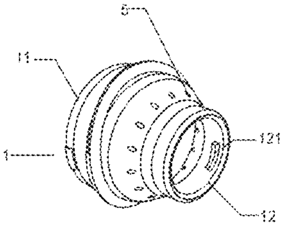
Figure 17A:
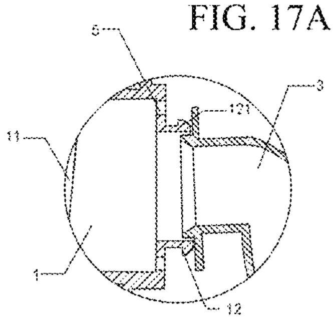
FIGS. 17A, 17B, and 17C are each a three-dimensional schematic diagram of yet another version of the connector and a cross-sectional view after the connector is assembled with the elbow in accordance with an embodiment.
Figure 17B:
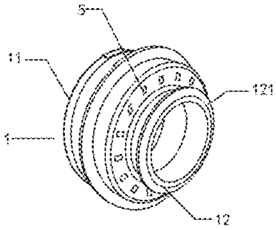
Figure 17C:
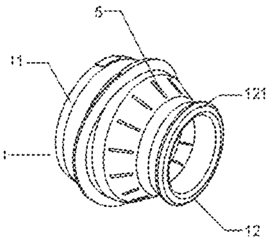
Figures 18A, 18B, 18C, 18D:
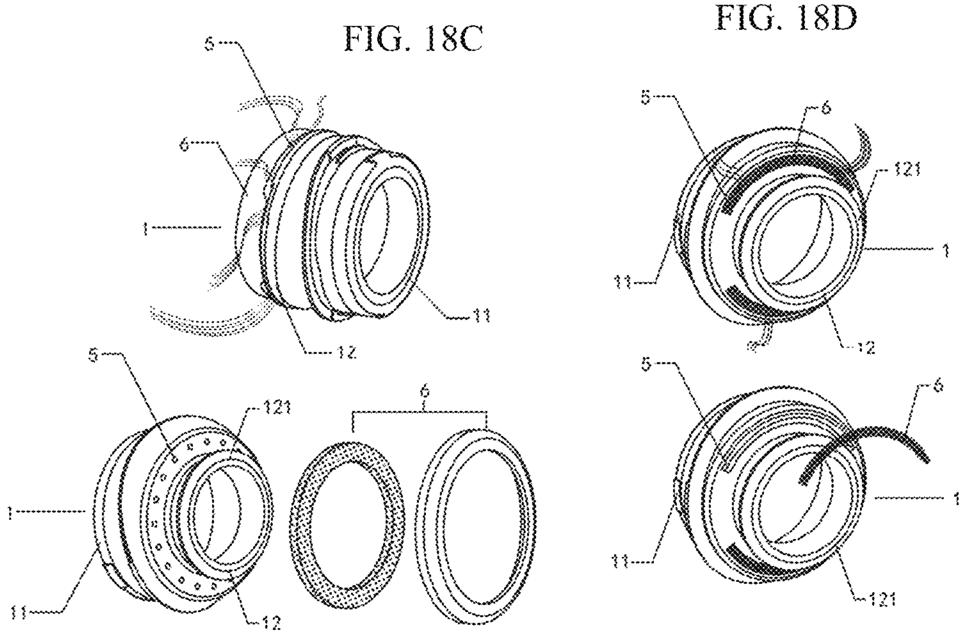
FIGS. 18A-18D are structural schematic diagrams of different forms of the connector in accordance with another embodiment.

In one embodiment, the noise reduction component 6 used to cover the exhaust port 5 on the connector 1 can have a mesh-like structure, a grille-like structure, or consist of separator elements with several micro-holes. The noise reduction component 6, which is used to cover the exhaust port 5 on the connector 1, can be made from materials such as polypropylene, polyethylene, polyester, nylon, or natural fabrics. See, e.g., FIGS. 15A-15D. Due to the placement of the exhaust port 5, connector 1 itself has a certain noise reduction function. The structure and shape of the component on the connector 1 used to create the exhaust port 5 have a significant impact on absorbing, isolating, or reducing the noise generated by the airflow. For example, FIG. 15A and FIG. 18B show noise reduction components 6 in a mesh-like structure made from polypropylene or polyethylene material. FIG. 15B demonstrates a noise reduction component 6 with a grille-like structure made from silicone material. FIG. 15C displays a separator element made from fabric with several micro-holes that is used to form the noise reduction component 6. FIG. 15D shows a separator element made from cotton with several micro-holes that is also used to create the noise reduction component 6. In the embodiment, the exhaust port 5, while providing noise reduction, contributes to a comfortable and peaceful treatment experience for patients. The design of noise reduction component 6 on the connector 1 helps improve overall treatment effectiveness and user satisfaction.

When the noise reduction component 6 covering the exhaust port 5 takes the form of a mesh, the total area of the exhaust port 5 can be at or between 3% to 90% of the inner and outer surface areas of the connector 1. The external outline shape of the exhaust port 5 includes, but is not limited to, circular, elliptical, semi-circular, and square shapes. The materials for the exhaust mesh can include, but are not limited to, polypropylene, polyethylene, polyester, nylon, and natural fabrics.

In another embodiment, the noise reduction component 6 includes an external connecting part. As shown in FIG. 18A. The noise reduction component 6 includes noise reduction material corresponding to the exhaust port 5 and an external connecting part fixed to the connector 1, which restricts the noise reduction material to the area of the exhaust port 5. The external connecting part is positioned on the side of the noise reduction material that faces away from the connector. The external connecting part is placed on one side of the noise-reduction material, the side that is back to the connector. The external connecting part is either snap-fitted to the connector 1 (the external connecting part is buckled to connector 1) or magnetically attached (by the coordination of positive and negative poles on the connector 1 and the external connecting part.

Embodiment 5

The disclosure discloses a connector 1 for a frame of a respirator, configured to connect to a face mask assembly and create a pathway for transmitting positive pressure air or breathable air. The connector 1, configured for a removable attachment to a frame in a face mask assembly by insertion or surface contact, includes a first interface end 11 for assembling with and communicating with a face mask, a second interface end 12 for assembling with and communicating with an elbow, and exhaust ports 5 that permeate an inner surface of the connector 1 and an outer surface of the connector 1 to communicate with an external environment to allow internal gas to flow out. Each exhaust port 5 is distributed by surrounding the annular passage 13 of the connector 1. The connector 1 has at least one of the following characteristics:

a volume ratio of the connector to the frame is at or between 1:1.8 to 1:14;

a length of the connector is at or between 1 to 100 mm; and a weight of the connector is at or between 1 to 5 grams.

In comparison to Embodiment 1, this embodiment further specifies the parameters of the connector 1 and the connection between connector 1 and the frame 4 becomes non-detachable. Preferably, the overall length of connector 1 can be approximately at or between 3 to 50 mm, providing sufficient contact area for connector 1 to connect to the frame 4, the face mask 2, and the elbow 3. Connector 1 can exhibit at least partial deformability, with basically no deformation in a static state and reversible, minor changes in shape when subjected to external forces. The design of connector in Embodiment 5 extends the lifespan of the connector 1 and accommodates the usage habits of different patients. The connector 1 can be constructed from one or two materials chosen from polycarbonate, polyethylene, polypropylene, and silicone. Furthermore, the outer diameter of the first interface end 11 is at or between 10 to 80 mm, while the outer diameter of the second interface end 12 is at or between 10 to 80 mm. The wall thickness of the connector 1 is at or between 0.3 to 5 mm. By controlling the wall thickness of the connector 1, it is possible to manage the overall weight of connector 1, making it lighter for patients to wear the face mask 2, when the connector 1 fits with the elbow 3 and mask 2. Additionally, in the embodiment, at least one end of the connector 1 includes a circular cross-section with an outer diameter of at or between 5 to 80 mm. The peripheral circumference where the connector 1 intersects with the frame 4 is smaller than the opening circumference of the frame 4 that accommodates the connector 1, which allows the connector 1 to smoothly pass through the central opening 40 of the frame 4 and securely mate with the frame 4. When the connector 1 is connected to the frame 4, at least a portion of the external wall of the connector 1 snugly fits against the inner wall of the frame 4, creating a sealed pathway for pressurized air.

Figure 19:
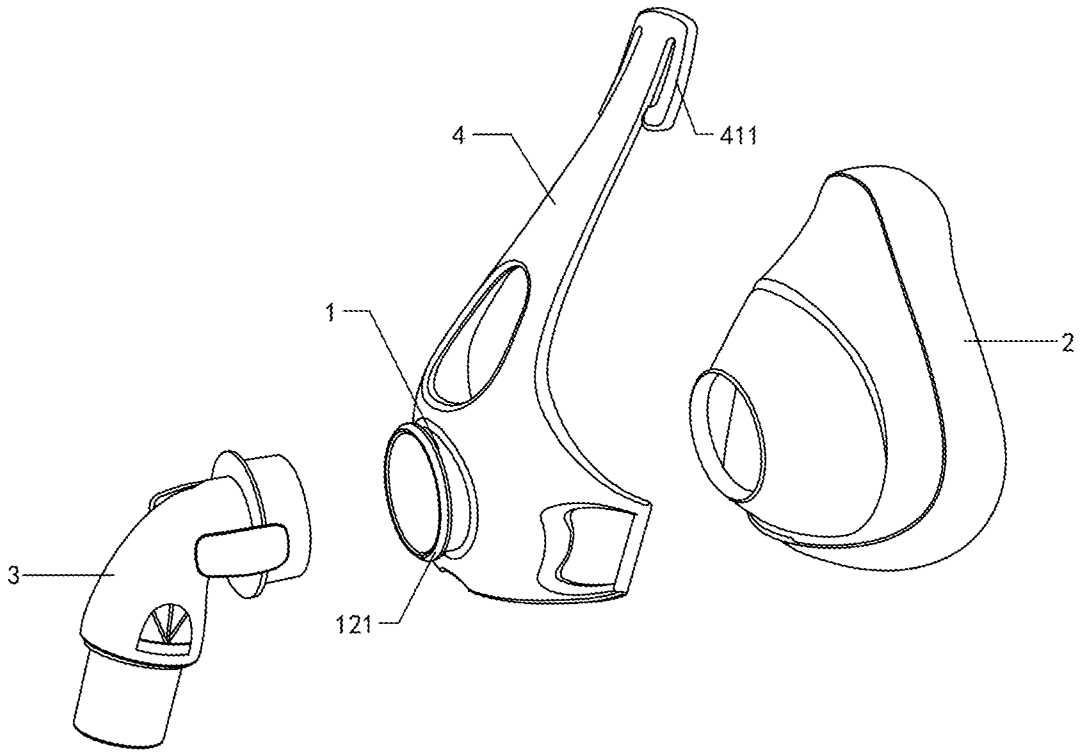
FIG. 19 is an exploded schematic diagram of the connector, frame, face mask, and elbow in accordance with another embodiment.

In this embodiment, the connector 1 is fixed to the frame 4 using either ultrasonic bonding (plastic welding technology) or adhesive. As shown in FIG. 19, connector 1 and the frame 4 provide an undetachable connection, ensuring a solid frame component for the patient. Both of these different methods, ultrasonic (plastic welding technology) or adhesive, serve the same purpose: to provide a reliable connection and ensure that the exhaust component does not come loose during use. The connector 1 and the frame 4 can also use an undetachable snap-fit.

The various technical features described in the above embodiment can be combined in any way. To keep the description concise, not all possible combinations of these technical features in the above embodiment have been described. However, as long as the combination of these technical features is not contradictory, it should be considered within the scope of this specification.

It should be noted that the above-mentioned embodiments only represent several ways of implementing the disclosure. While the descriptions are relatively specific and detailed, the information provided in the document does not imply a limitation on the scope of the patent. It should be pointed out that, for those skilled in the field of face mask assembly, various modifications and improvements can be made without departing from the basic concept of the disclosure, which are all within the scope of protection of the disclosure. Therefore, the scope of protection of the patent for the disclosure should be determined by the appended claims.

It must be noted that as used herein and in the appended claims, the singular forms “a”, “an”, and “the” include their plural equivalents, unless the context clearly dictates otherwise.

The invention claimed is:

1. A face mask assembly, comprising:

a frame;

a face mask;

an elbow; and a modular connector configured to:

connect the frame with the face mask and to the elbow to create a pathway to transmit positive pressure air or breathable air, the connector unitarily comprising:

a fitting to detachably connect with the frame;

a first interface end to assemble with and connect to the face mask; and a second interface end to assemble with and connect to the elbow, and wherein an annular passage connects the first interface end and the second interface end to allow the positive pressure air or breathable air to pass through and enter an airway, wherein an axis of the connector coincides with an axis of a gas outlet at the elbow, wherein the connector passes through a central opening of the frame and is fixedly connected to the frame to prevent sliding or rotation of the connector relative to the frame;

wherein the first and second interface ends are unitarily formed as the connector and a length of the connector is at or between 3 to 50 mm;

wherein an inner diameter of the connector does not exceed 80 mm; and wherein a minimum ratio between an opening area of the second interface end and an outer surface area of the frame is 1:20.

2. The face mask assembly according to claim 1, wherein the frame is made from a rigid or deformable material.

3. The face mask assembly according to claim 1, wherein an overall length of the connector is greater than a wall thickness of the central opening of the frame.

4. The face mask assembly according to claim 1, wherein at least a portion of the frame is configured to contact a face; and wherein the frame is configured to cover at least a portion of the face mask when the frame and the face mask are connected.

5. The face mask assembly according to claim 1, further comprising:

a gasket provided on the connector between the first interface end and the second interface end, wherein a notch is provided on an edge of the central opening of the frame on a side facing the second interface end of the connector, and wherein the gasket is embedded in the notch when the connector is assembled with the frame.

6. The face mask assembly according to claim 5, wherein an outer surface of the first interface end includes a first protrusion, and an outer surface of the second interface end includes a second protrusion, wherein a positioning protrusion is provided between the first protrusion and the gasket, and the fitting includes a positioning groove that corresponds to a concave-convex shape of an inner edge of the central opening of the frame provided between the positioning protrusion and the gasket, and wherein at least one side of the positioning protrusion that is near the second interface end or away from the second interface end is a sloped surface.

7. The face mask assembly according to claim 6, wherein one or more interlocking interfaces that concavely and convexly adapt with the second protrusion to form a sealed connection are provided at the central opening of the frame.

8. The face mask assembly according to claim 1, wherein the first interface end is detachably connectable to the face mask, and the second interface end is detachably connectable to the elbow, with the connector connecting to the elbow and to the face mask to form a seal.

9. The face mask assembly according to claim 1, wherein an outer periphery of the second interface end is smaller than an outer periphery of the first interface end.

10. The face mask assembly according to claim 1, wherein a central axis of the connector is configured to form an angle of at or between 10° to 90° with a symmetrical axis of the frame.

11. A face mask assembly, comprising:

a frame;

a face mask;

an elbow; and a modular connector configured to:

fixedly connect to the frame by passing through a central opening of the frame to prevent sliding or rotation of the connector relative to the frame, and create a pathway to transmit positive pressure air or breathable air, wherein the connector unitarily comprises:

a first interface end to be assembled with and to connect to the face mask, a second interface end to be assembled with and to connect to the elbow, and at least one exhaust port that permeates an inner surface of the connector and an outer surface of the connector to connect to an external environment to allow internal gas to flow out, and wherein an outer periphery of a section in which the connector fits with the frame is smaller than an inner periphery of the central opening of the frame through which the connector passes; and wherein each of the at least one exhaust port has different diameters at two ends of each of the at least one exhaust port.

12. The face mask assembly according to claim 11, wherein the at least one exhaust port is distributed evenly or unevenly along an annular passage of the connector.

13. The face mask assembly according to claim 11, wherein an angle between an axis of each of the at least one exhaust port and an axis of the connector is at or between 0° to 90°.

14. The face mask assembly according to claim 11, wherein each of the at least one exhaust port is configured to be circular or semicircular.

15. A face mask assembly, comprising:

a frame;

a face mask;

an elbow; and a modular connector configured to:

detachably connect to the elbow of the face mask assembly;

create a pathway to transmit positive pressure air or breathable air; and fixedly connect to the frame in the face mask assembly by passing through a central opening of the frame to prevent sliding or rotation of the connector relative to the frame, wherein the connector unitarily comprises:

a first interface end to be assembled with and to connect to the face mask, a second interface end to be assembled with and to connect to the elbow, and exhaust ports that permeate an inner surface of the connector and an outer surface of the connector to connect to an external environment to allow internal gas to flow out, and wherein each of the exhaust ports is distributed along an annular passage of the connector; and wherein the outer surface of the connector connects to a noise reduction component, which includes a noise reduction material set for a corresponding one of the exhaust ports, with the noise reduction material having at least one of the following characteristics:

a density of the noise reduction material being at or between 0.8 to 1.8 g/cm$^3$; or a thickness of the noise reduction material being at or between 0.1 to 0.5 mm.

16. The face mask assembly according to claim 15, wherein the noise reduction material is a mesh-like structure or a cotton fluff structure.

17. The face mask assembly according to claim 15, wherein the noise reduction material includes cotton, nylon, or natural fabric.

18. The face mask assembly according to claim 15, wherein the noise reduction component is a mesh-like structure, a grille-like structure, or a partition with several micro-holes; and wherein the noise reduction component which is configured to cover each of the exhaust ports on the connector is made from polypropylene, polyethylene, polyester, nylon, or natural fabric.

19. The face mask assembly according to claim 15, wherein the noise reduction component includes an external connecting part to connect to the connector through a snap-fitting or a magnetic attraction.

20. A face mask assembly, comprising:

a frame;

a face mask;

an elbow, and a modular connector configured to:

connect the frame with the face mask and to the elbow to create a pathway to transmit positive pressure air or breathable air, fixedly connect to the frame by passing through a central opening of the frame to prevent sliding or rotation of the connector relative to the frame;

wherein the modular connector unitarily comprises:

a first interface end to be assembled with and to connect to the face mask, a second interface end to be assembled with and to connect to the elbow, and exhaust ports that permeate an inner surface of the connector and an outer surface of the connector to connect to an external environment to allow internal gas to flow out, and wherein each of the exhaust ports is distributed by surrounding an annular passage of the connector; and wherein the connector has at least one of the following characteristics:

a volume ratio of the connector to the frame being at or between 1:1.8 to 1:14;

the first and second interface ends are integrally formed as the connector and a length thereof the connector being at or between 1 to 100 mm; or a weight of the connector being at or between 1 and 5 grams.

21. The face mask assembly according to claim 20, wherein an outer diameter of the first interface end is at or between 10 to 80 mm, an outer diameter of the second interface end is at or between 10 to 80 mm, and a wall thickness of the connector is at or between 0.3 to 5 mm.

22. The face mask assembly according to claim 20, wherein at least one end section of the connector includes a circular cross-section.

23. The face mask assembly according to claim 20, wherein the connector is at least partially deformable.

24. The face mask assembly according to claim 20, wherein the connector is made from one or two materials from polycarbonate, polyethylene, polypropylene, or silicone.

25. The face mask assembly according to claim 20, wherein the connector is detachably connectable to the frame through a snap-fitting, a rotary fitting, or a magnetic attraction;

wherein the connector is connectable to the face mask by a snap-fitting, a rotary fitting, or a magnetic attraction; and wherein the connector is connectable to the elbow through a snap-fitting, a ball socket rotation, or a hinge connection.

* * * * *